United States Patent [19]

Kubo et al.

[11] Patent Number: 4,636,516

[45] Date of Patent: Jan. 13, 1987

[54] 3,5-DI-TERT-BUTYL-4-HYDROXYPHENYL-SUBSTITUTED HETEROCYCLIC COMPOUNDS

[75] Inventors: Kazuo Kubo, Saitama; Yasuo Isomura; Shuichi Sakamoto, both of Tokyo; Hiroshige Homma, Saitama, all of Japan

[73] Assignee: Yamanouchi Pharmaceutical Co., Ltd., Tokyo, Japan

[21] Appl. No.: 347,982

[22] Filed: Feb. 11, 1982

[30] Foreign Application Priority Data

Feb. 19, 1981 [JP] Japan .................................. 56-23515
Apr. 21, 1981 [JP] Japan .................................. 56-59990
Oct. 2, 1981 [JP] Japan .................................. 56-157010

[51] Int. Cl.$^4$ .................. C07D 233/42; C07D 277/36; A61K 31/415; A61K 31/425
[52] U.S. Cl. ..................................... 514/365; 514/369; 514/370; 514/374; 514/376; 514/377; 514/398; 514/400; 548/183; 548/184; 548/186; 548/190; 548/193; 548/203; 548/229; 548/233; 548/235; 548/313; 548/315; 548/321; 548/337; 548/342; 548/154
[58] Field of Search ............... 548/183, 184, 186, 190, 548/193, 203, 229, 233, 235, 313, 315, 321, 337, 548/342; 514/374, 376, 377, 369, 370, 365, 400, 398

[56] References Cited

U.S. PATENT DOCUMENTS 4,044,019 8/1977 Schmidt ............................. 548/313

Primary Examiner—Robert Gerstl
Attorney, Agent, or Firm—Burgess, Ryan & Wayne

[57] ABSTRACT

Novel 3,5-di-tert-butyl-4-hydroxyphenyl-substituted heterocyclic compounds shown by the formula

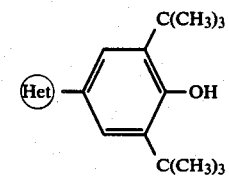

wherein (Het) — represents a specific heterocyclic group and the salts thereof.

The compounds have an anti-inflammatory, an antipyretic, an analgesic, an anti-arthritic, and an immunoregulatory activity. Hence, they are particularly useful as an antirheumatics.

16 Claims, No Drawings

3,5-DI-TERT-BUTYL-4-HYDROXYPHENYL-SUBSTITUTED HETEROCYCLIC COMPOUNDS

DETAILED DESCRIPTION OF THE INVENTION

This invention relates to novel 3,5-di-tert-butyl-4-hydroxyphenyl-substituted heterocyclic compounds. More particularly, the invention relates to the 3,5-di-tert-butyl-4-hydroxyphenyl-substituted heterocyclic compounds shown by formula I and their salts;

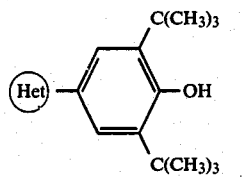

wherein — represents a heterocyclic group shown by the formula

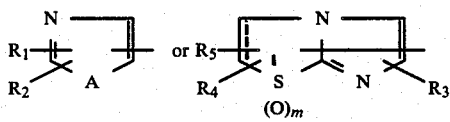

[wherein $R_1$ and $R_2$, which may be the same or different, each represents a hydrogen atom, a lower alkyl group, a lower aralkyl group, an aryl group, a lower alkoxy-substituted aryl group, or a group shown by —O—Z,

or —NH—Z (wherein Z represents a hydrogen atom, a lower alkyl group, a carboxy lower alkyl group, a lower alkoxycarbonyl lower alkyl group, a lower aralkyl group, or an aryl group and n represents 0, 1, or 2); A represents an oxygen atom, a sulfur atom, an imino group, a lower alkylimino group, or a 3,5-di-tert-butyl-4-hydroxyphenacylimino group

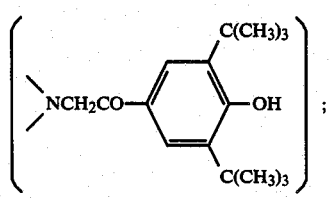

$R_3$, $R_4$, and $R_5$, which may be the same or different, each represents a hydrogen atom, a halogen atom, a lower alkyl group, a hydroxy lower alkyl group, an amino lower alkyl group, an aryl group, a lower alkoxy-substituted aryl group, a lower alkanoyl group, a lower alkylthio group, a lower alkoxy group, a lower aralkyl group, a cyano group, or a thiocyanato group; m represents 0, 1, or 2; and the dotted line means the presence or absence of a double bond). The terminology throughout the specification and the claims of this invention is as follows:

The term "lower" means a straight or branched carbon chain of 1-6 carbon atoms. Therefore, for example, "lower alkyl group" includes methyl group, ethyl group, propyl group, isopropyl group, butyl group, isobutyl group, tert-butyl group, heptyl group, hexyl group, etc.; "lower aralkyl group" includes benzyl group, phenethyl group, etc.; "lower alkoxy group" includes methoxy group, ethoxy group, propoxy group, isopropoxy group, butoxy group, hexyloxy group, etc.; "lower alkylthio group" includes methylthio group, ethylthio group, propylthio group, isopropylthio group, etc.; and "lower alkanoyl group" includes formyl group, acetyl group, propionyl group, isopropionyl group, butyryl group, hexanoyl group, etc. Also, the term "amino" in "amino lower alkyl group" means not only amino group but also mono- or di-alkylamino group such as methylamino group, dimethylamino group, diethylamino group, etc., and cyclic amino group such as morpholino group, pyrrolidino group, piperidino group, piperazino group, 4-lower alkyl-piperazino group, etc. Furthermore, the term "aryl group" includes phenyl group, naphthyl group, etc., and the term "halogen atom" includes chlorine atom, bromine atom, iodine atom, fluorine atom, etc.

Then, as the salts of the compounds of this invention shown by formula I, there are pharmaceutically acceptable acid addition salts, for example, acid addition salts of an inorganic acid such as hydrochloric acid, hydrobromic acid, sulfuric acid, nitric acid, phosphoric acid, etc.

The compounds of this invention shown by formula I have an anti-inflammatory, an anti-pyretic, analgesic, an antiarthritic and an immuno regulatory activity. Hence they are novel compounds particularly useful as an antirheumatic.

That is, since the compounds of this invention shown by formula I show a therapeutic and prophylactic effect on adjuvant-induced arthritis which is considered to be an animal model of human rheumatism and further have analgesic and anti-inflammatory activities as well as a prostaglandins formation inhibiting activity as a biochemical activity, the compounds of this invention are considered to be useful for the therapeutic and prophylaxis of human rheumatic disease. Moreover, the compounds of this invention shown by formula I suppress remarkably Coomb's type III (Arthus reaction) and type IV (delayed type hypersensitivity) allergic reactions as well as have a lipoxigenase suppressing activity and a property as a radical scavenger, which have never been attained by conventional nonsteroidal acidic anti-inflammatory antirheumatics represented by indomethacin and diclofenac. Therefore, the compounds of this invention are particularly useful as antirheumatics having new mechanism.

The 1st feature of the chemical structure of the compounds of this invention shown by formula I is that the compounds belong to a nonsteroidal nonacidic anti-inflammatory agent, and different from conventional nonsteroidal acidic anti-inflammatory agents such as indomethacin and diclofenac. The 2nd feature is in the point that the heterocyclic ring of the heterocyclic compound is directly substituted by a 3,5-di-tert-butyl-4-hydroxyphenyl group. The 3rd feature is in the point that the substituted heterocyclic ring itself is a specific heterocyclic ring. Practically, the heterocyclic ring in the heterocyclic compound of this invention is

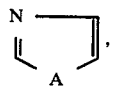

i.e., an imidazole ring, a thiazole ring, or an oxazole, or

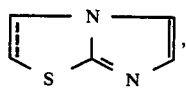

i.e., a (2,3-dihydro)imidazo[2.1-b]thiazole ring.

As heterocyclic compounds the heterocyclic ring of which is directly substituted by a 3,5-di-tert-butyl-4-hydroxyphenyl group, there are known, for example, 2-(3,5-di-tert-butyl-4-hydroxyphenyl)benzoxazole compounds and 2-(3,5-di-tert-butyl-4-hydroxyphenyl)-benzothiazole compounds (West German Offenlegungsshrift No. 2,008,414) 2-(3,5-di-tert-butyl-4-hydroxyphenyl)-1,3-diphenylimidazolidine compounds (Belgian Pat. No. 807,140); and 2-[2-(3.5-di-tert-butyl-4-hydroxyphenyl)-5-ethoxy-4-thiazolyl]acetic acid (Japanese Pat. Appln. Laid Open No. 7669/'78). The benzoxazole compounds and the benzothiazole compounds are used as an antioxidant and the imidazolidine compounds are used as intermediates for plant protecting agents and dyes. The last acetic acid compound is suggested to be used as an anti-thrombotic agent, a hypolipaemic agent, and an anti-inflammatory agent. About the acetic acid compound, the use as an anti-inflammatory agent is suggested as described above but there is no disclosure about the practical pharmacological effect of the compound as an anti-inflammatory agent and also the chemical structure of the acetic acid compound is a heterocyclic ring-substituted acetic acid derivative, which belongs to a nonsteroidal acidic anti-inflammatory agent and hence differs from the compounds of this invention shown by formula I in chemical structure.

The preferred compound group of the compounds of this invention shown by formula I is compounds having the heterocyclic ring shown by

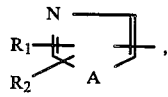

that is the 3,5-di-tert-butyl-4-hydroxyphenyl-substituted heterocyclic compounds shown by the formula Ia

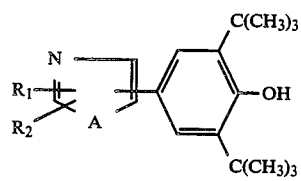

wherein $R_1$, $R_2$, and A have the same significance as defined above.

The particularly preferred compounds in the foregoing heterocyclic compounds are as follows;

4-(3,5-di-tert-butyl-4-hydroxyphenyl)-5-methyl-2-oxo-4-imidazoline, 4-(3,5-di-tert-butyl-4-hydroxyphenyl)-5-ethyl-2-oxo-4-imidazoline 4-(3,5-di-tert-butyl-4-hydroxyphenyl)-5-methyl-2-methylthioimidazole.

4-(3,5-di-tert-butyl-4-hydroxyphenyl)-5-methylimidazole, 4-(3,5-di-tert-butyl-4-hydroxyphenyl)-2-mercaptothiazole, 4-(3,5-di-tert-butyl-4-hydroxyphenyl)-2-methylthiothiazole, 4-(3,5-di-tert-butyl-4-hydroxyphenyl)-5-ethylimidazole, and 4-(3,5-di-tert-butyl-4-hydroxyphenyl)-5-ethyl-2-methylthioimidazole.

Other preferred compound groups of the compounds of this invention shown by formula I is the compounds having the heterocyclic group shown by

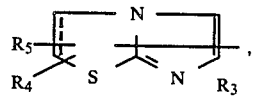

that is, the 3,5-di-tert-butyl-4-hydroxyphenyl-substituted heterocyclic compounds shown by the formula Ib;

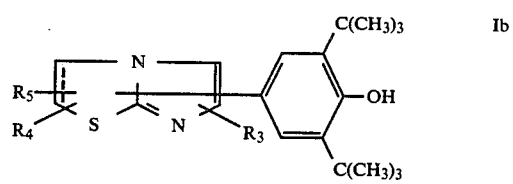

wherein $R_3$, $R_4$, and $R_5$ have the same significance as defined above. The particularly preferred compounds in the foregoing heterocyclic compounds are as follows;

6-(3,5-di-tert-butyl-4-hydroxyphenyl)5-methyl-2,3-dihydroimidazo[2,1-b]thiazole, 6-(3,5-di-tert-butyl-4-hydroxyphenyl)-2,3-dihydroimidazo[2,1-b]thiazole 1-oxide, 6-(3,5-di-tert-butyl-4-hydroxyphenyl)-2,3-dihydroimidazo[2,1-b]thiazole 1,1-dioxide, and 6-(3,5-di-tert-butyl-4-hydroxyphenyl)-2,3-dihydroimidazo[2,1-b]thiazole.

In addition, there are prototropic isomers on the compounds of this invention shown by formula I. For example, in the compounds of this invention shown by formula Ia wherein $R_1$ is

(wherein n is 0 and Z is a hydrogen atom) or $R_1$ is —OZ (wherein Z is a hydrogen atom), there are following prototropic isomers;

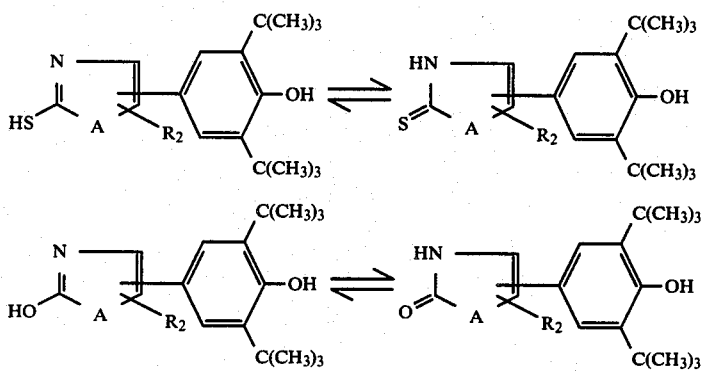

The compounds of this invention shown by formula I can be prepared by the following methods:

(A) The compounds of this invention shown by formula I wherein 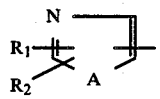 is the heterocyclic group shown by

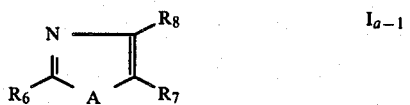

(wherein $R_1$, $R_2$, and A have the same significance as defined above), that is the compound shown by formula Ia can be shown by formula Ia-1

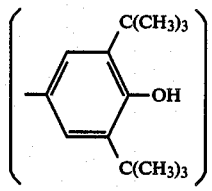  Ia-1 wherein one of $R_6$, $R_7$, and $R_8$ represents a 3,5-di-tert-butyl-4-hydroxyphenyl group $$\left\{ \begin{array}{c} \text{C(CH}_3)_3 \\ \text{—} \phantom{x} \text{—OH} \\ \text{C(CH}_3)_3 \end{array} \right\}$$

and others of them have the same significance as $R_1$ and $R_2$, and A has the same significance as defined above, and the compound can be prepared by the following method:

(i) First production method:

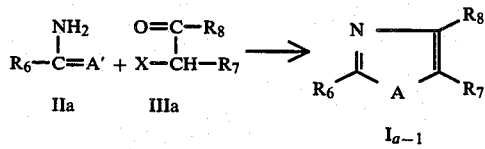

wherein A' represents an oxygen atom, a sulfur atom, an imino group or a lower alkylimino group; X represents a halogen atom; and $R_6$, $R_7$, and $R_8$ have the same significance as defined above.

That is, the compound of this invention shown by formula Ia-1 can be prepared by reacting the compound shown by formula IIa (i.e., urea, thiourea, amidine, amide, thioamide, and amidothiocarbonic acid derivatives) with the α-halocarbonyl compound shown by formula IIIa. This reaction is performed by heating the compound of formula IIa and a corresponding amount of the compound of formula IIIa in situ or in a proper solvent such as methanol, ethanol, toluene, dimethylformamide, acetone, chloroform, methyl ethyl ketone, ethyl acetate, methyl cellosolve, ethyl cellosolve, digryme acetonitrile, etc. The reaction temperature and the reaction time are suitably determined according to the kinds of starting materials and solvent used. In addition, the compound of formula IIa may be used for the reaction as a salt thereof, such as a hydrochloride of an amidine derivative or ammonium amidodithiocarbonate.

Furthermore, when in the method, cyanourea ($NH_2CONHCN$) is reacted with the α-halocarbonyl compound of formula IIIa and then the product is hydrolyzed, the compound of formula $I_{a-1}$ wherein $R_6$ is a hydroxyl group and A is an imino group, i.e., the compounds of this invention shown by the formula

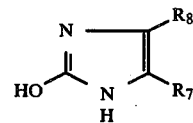

wherein $R_7$ and $R_8$ have the same significance as defined above can be produced.

(ii) Second production method:

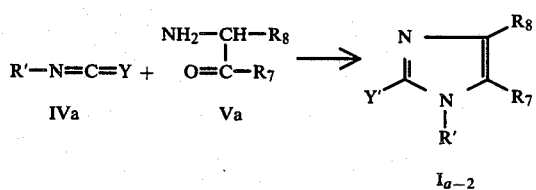

wherein R' represents a hydrogen atom or a lower alkyl group; Y' represents a hydroxyl group or a mercapto group; Y represents an oxygen atom or a sulfur atom; and $R_7$ and $R_8$ have the same significance as defined above.

That is, the compounds of this invention shown by formula $I_{a-1}$ wherein A is an imino group or a lower alkylimino group and $R_6$ is a hydroxyl group or a mercapto group, i.e., the compounds shown by formula $I_{a-2}$ can be prepared by reacting the compound shown by formula IVa (i.e., isocyanic acid, isothiocyanic acid, and the lower alkyl-substituted derivatives of them) or the alkali metal salt thereof with the α-aminocarbonyl compound shown by formula Va or the salt thereof. In the case of using the alkali metal salt of isocyanic acid or isothiocyanic acid, the reaction is performed in a solvent such as alcohol, aqueous alcohol, etc., with the addition of an acid such as hydrochloric acid, etc., at room temperature or under heating. In the case of heating, the reaction may be performed under refluxing at about the boiling point of the solvent used.

Also, in the case of using the lower alkyl-substituted derivative of isocyanic acid or isothiocyanic acid, the reaction is performed in a basic solvent such as pyridine, etc., at room temperature or under heating.

In addition, the compounds of this invention shown by formula $I_{a-2}$ wherein Y' is a mercapto group, i.e., the compounds shown by the formula

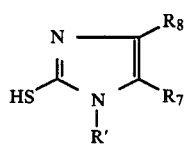

wherein R', $R_7$, and $R_8$ have the same significance as defined above can be prepared by reacting the compound shown by the formula

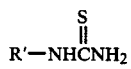

with the compound shown by

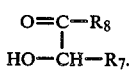

(iii) Other production methods:
(1) oxidation $R_7$, $R_8$, A, and Z have the same significance as defined above.

The oxidation method (1) is a method of producing the compound of this invention shown by formula $I_{a-1}$ wherein $R_6$ is

and n is 1 or 2, i.e., the S-oxide compound shown by formula $I_{a-4}$. The S-oxide compound can be prepared by reacting the corresponding compound of this invention shown by formula $I_{a-1}$ wherein $R_6$ is

and n is 0, i.e., the thio compound shown by formula $I_{a-3}$ with an oxidizing agent in a solvent such as acetic acid, chloroform, 1,2-dimethoxyethane, etc., according to an ordinary manner. As the oxidizing agent, 10–40% hydrogen peroxide, perbenzoic acid, m-chloroperbenzoic acid, etc., is usually used. In this case, by suitably selecting the reaction conditions such as the reaction time, reaction temperature, the amount of the oxidizing agent, etc., a desired monooxide compound (n'=1) or dioxide compound (n'=2) can be obtained.

The alkylation method (2) is a method of producing the compound of this invention shown by formula $I_{a-1}$ wherein $R_6$ is —S—Z,
$(O)_n$ n is 0, and Z is a lower alkyl group, a carboxy lower alkyl group, a lower alkoxycarbonyl lower alkyl group, or a lower aralkyl group, i.e., the alkylthio compound shown by formula $I_{a-6}$. The alkylthio compound can be produced by alkylating the compound of this invention shown by formula $I_{a-1}$ wherein $R_6$ is

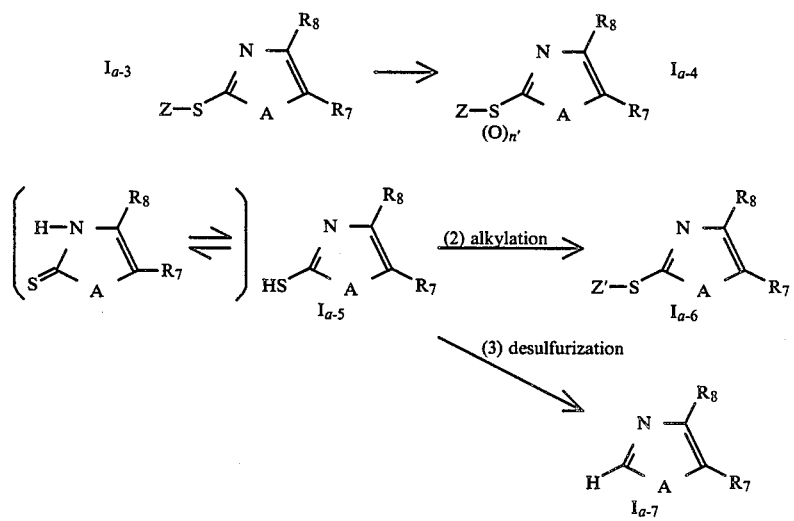

wherein n' represents 1 or 2; Z' represents a lower alkyl group, a carboxy lower alkyl group, a lower alkoxycarbonyl lower alkyl group, or a lower aralkyl group; and —S—Z,
$(O)_n$ Z is a hydrogen atom, and n is 0, i.e., the mercapto (or thioxo) compound shown by formula $I_{a-5}$ with an alkylating agent in a solvent such as methanol, acetone, dimethylformamide, etc., by an ordinary manner. As the alkylating agent used in the reaction, there are alkyl halides or aralkyl halides such as methyl iodide, ethyl bromide, α-bromopropionic acid, α-bromoacetic acid, ethyl α-bromopropionate, benzyl bromide, phenethyl iodide, etc., and dialkyl sulfates such as dimethyl sulfate, diethyl sulfate, etc.

The desulfurization reaction (3) is a method of producing the compound of this invention shown by formula $I_{a-1}$ wherein $R_6$ is a hydrogen atom, i.e., the compound shown by formula $I_{a-7}$. The compound can be produced by desulfurizing the corresponding mercapto (or thioxo) compound shown by formula $I_{a-5}$ according to a conventional manner, for example, by treating the compound with a Raney nickel catalyst.

(B) The compounds of this invention shown by formula I wherein (Het) is the herocyclic group shown by

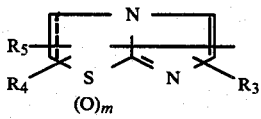

wherein $R_3$, $R_4$, $R_5$, and m have the same significance as defined above, that is, the compound shown by formula Ib can be shown by formula $I_{b-1}$

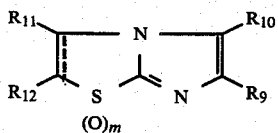

wherein one of $R_9$, $R_{10}$, $R_{11}$, and $R_{12}$ represents a 3,5-ditert-butyl-4-hydroxyphenyl group

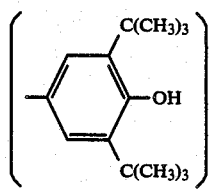

others have the same significance as $R_3$, $R_4$, and $R_5$; and m and the dotted line have the same significance as defined above, and the compound can be prepared by the following methods.

(i) First production method:

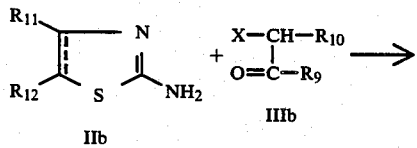

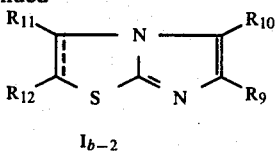

wherein X represents a halogen atom and $R_9$, $R_{10}$, $R_{11}$, $R_{12}$, and the dotted line have the same significance as defined above.

The compounds of this invention shown by formula $I_{b-1}$ wherein m is 0, i.e., the compounds shown by formula $I_{b-2}$ can be prepared by reacting the 2-aminothiazoline derivative or 2-aminothiazole derivative shown by formula IIb with the α-halocarbonyl compound shown by formula IIIb. The reaction is performed by heating the compound of formula IIb and the corresponding amount of the compound of formula IIIb in situ or in a proper solvent such as methanol, ethanol, toluene, dimethylformamide, acetone, chloroform, methyl ethyl ketone, ethyl acetate, methyl cellosolve, ethyl cellosolve, diagryme, acetonitrile, etc. The reaction temperature and the reaction time are properly selected according to the kinds of the solvent and the starting materials used, but the reaction is advantageously performed under refluxing.

(ii) Second production method

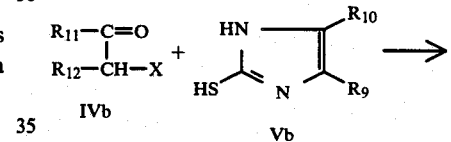

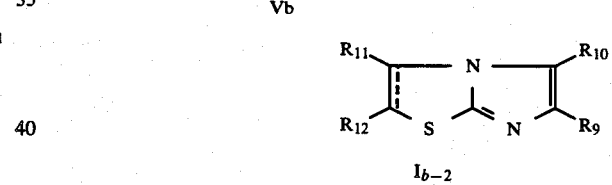

wherein $R_9$, $R_{10}$, $R_{11}$, $R_{12}$, X, and the dotted line have the same significance as defined above.

The compound shown by formula $I_{b-2}$ can be also prepared by reacting the α-halocarbonyl compound shown by formula IVb and the 2-mercaptoimidazole derivative shown by formula Vb or a salt thereof, e.g., an alkali metal salt thereof. The reaction is performed by reacting the compound of formula IVb with the corresponding amount of the compound of formula Vb or an alkali metal salt thereof in situ or in a proper solvent such as methanol, ethanol, toluene, dimethylformamide, acetone, chloroform, methyl ethyl ketone, ethyl acetate, methyl cellosolve, ethyl cellosolve, digryme, acetonitrile, etc. The reason usually proceeds at room temperature but may be performed under heating. The reaction time is properly determined according to the kinds of the solvent and the starting materials used. When the compound of formula Vb is used as it is , i.e., not as an alkali metal salt thereof, it is preferred that the compound is previously reacted with a alkali metal alcoholate to form a corresponding alkali metal salt and then the alkali metal salt is reacted with the compound of formula IVb.

This reaction is considered to proceed via an intermediate shown by formula VIb

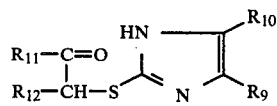 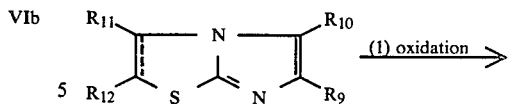

wherein $R_9$, $R_{10}$, $R_{11}$, and $R_{12}$ have the same significance as defined above, and if necessary, the intermediate can be isolated. The intermediate of formula VIb can be converted into the compound of formula $I_{b-2}$ by the treatment with an acid such as hydrochloric acid, acetic acid, etc., or phosphorus oxychloride.

In addition, by using the dihalogenoethane derivative shown by formula $IV_{b-1}$

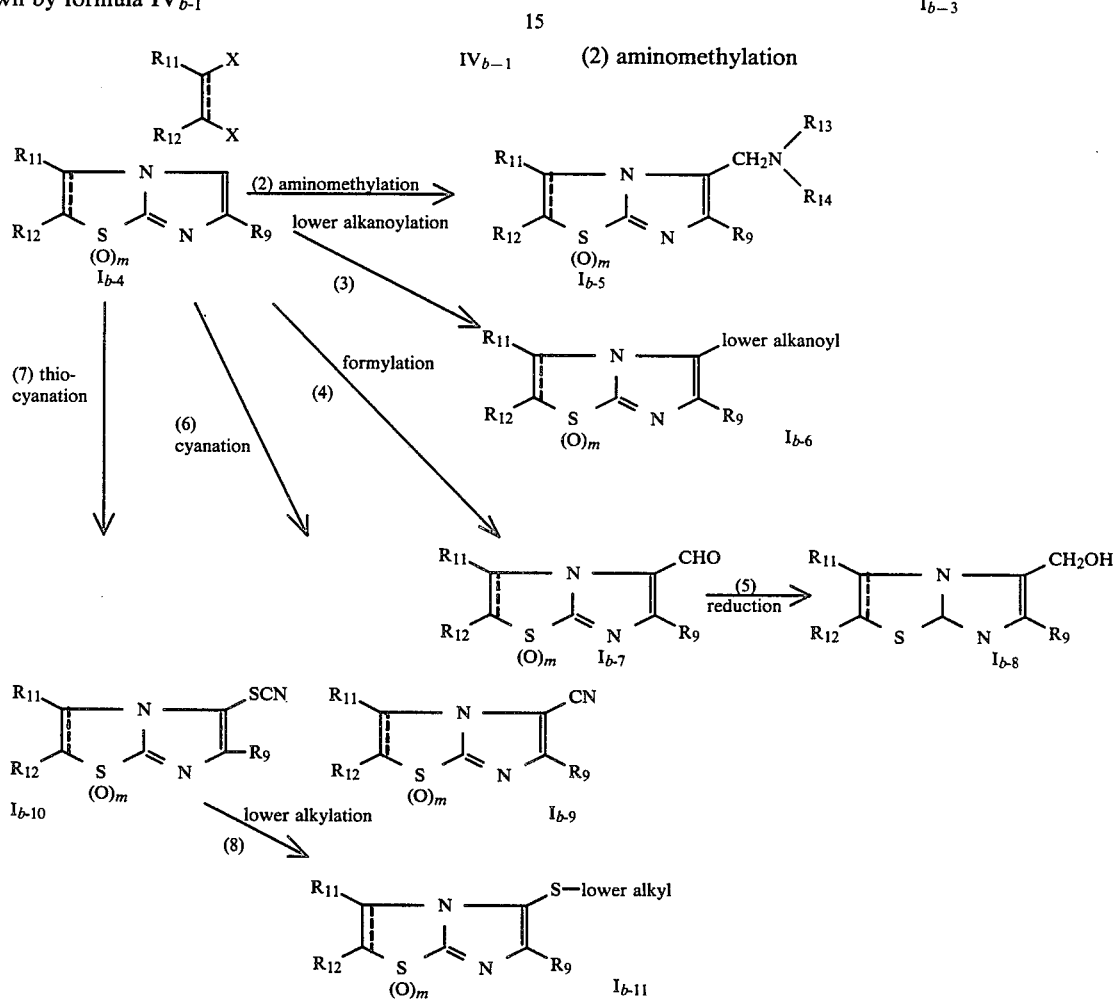

wherein $R_{11}$, $R_{12}$, and X have the same significance as defined above, in place of the α-halocarbonyl compound used in the starting material in the production method, the compounds of formula $I_{b-2}$ can be prepared.

(iii) Other production method:

wherein m' represents 1 or 2; $R_{13}$ and $R_{14}$ each represents a hydrogen atom, a lower alkyl group, or they may combine with each other to form a cyclic amino group; and $R_9$, $R_{10}$, $R_{11}$, $R_{12}$, m, and the dotted line have the same significance as defined above.

The oxidation method (1) is a method of producing the compounds of this invention shown by formula $I_{b-1}$ wherein m is 1 or 2, i.e., the S-oxide compound shown by formula $I_{b-3}$. The S-oxide compound can be prepared by reacting the corresponding thio compound of foregoing formula $I_{b-2}$ with an oxidizing agent in a solvent such as chloroform, 1,2-dimethoxyethane, acetic acid, etc., according to a conventional method. As the oxidizing agent, 10–40% hydrogen peroxide, perbenzoic acid, m-chloroperbenzoic acid, etc., is usually used. In this case, by properly selecting the reaction conditions such as the reaction time, the reaction temperature, the amount of the oxidizing agent, etc., the desired monooxide compound (m'=1) or dioxide compound (m'=2) can be obtained.

The aminomethylation method (2) is a method of producing the compound of this invention shown by formula $I_{b-1}$ wherein $R_{10}$ is an aminomethyl group, i.e., the aminomethyl compound shown by formula $I_{b-5}$. The aminomethylation is performed by reacting the compound shown by formula $I_{b-1}$ wherein $R_{10}$ is a hydrogen atom, i.e., the compound shown by formula $I_{b-4}$ with formaldehyde with the amine shown by

according to a Mannich reaction.

The lower alkanoylation method (3) is a method of producing the compounds of this invention shown by formula $I_{b-1}$ wherein $R_{10}$ is a lower alkanoyl group, i.e., the lower alkanoyl compound shown by formula $I_{b-6}$. The lower alkanoyl compound can be prepared by reacting the compound shown by formula $I_{b-4}$ with a lower alkanoyl halide such as acetyl chloride, etc., and an acid anhydride such as acetic anhydride, etc., according to a conventional method.

In addition, the lower alkanoyl compounds shown by formula $I_{b-6}$ wherein the lower alkanoyl group is a formyl group, i.e., the formyl compounds shown by formula $I_{b-7}$ can be also prepared by reacting the compound shown by formula $I_{b-4}$ with a complex (Vilsmeier reagent) of dimethylformamide (DMF) according to an ordinary manner and phosphorus oxychloride or oxalyl chloride and then hydrolyzing the reaction product. This method is the foregoing formylation method (4).

The reduction method (5) is a method of producing the compounds of this invention shown by formula $I_{b-1}$ wherein $R_{10}$ is a hydroxymethyl group, i.e., the hydroxymethyl compound shown by formula $I_{b-8}$. The hydroxymethyl compound can be produced by reducing the foregoing formyl compound of formula $I_{b-7}$ with a reducing agent such as sodium borohydride.

The cyanation method (6) is a method of producing the compounds of this invention shown by formula $I_{b-1}$ wherein $R_{10}$ is a cyano group, i.e., the nitrile compound shown by formula $I_{b-9}$. The nitrile compound can be produced by reacting the compound shown by formula $I_{b-4}$ with a Vilsmeier reagent as in the foregoing formylation method (4) according to a conventional method and then reacting the reaction product with hydroxyamine.

The thiocyanation method (7) is a method of producing the compounds of this invention shown by formula $I_{b-1}$ wherein $R_{10}$ is a thiocyante (—SCN) group, i.e., the thiocyanate compound shown by formula $I_{b-10}$. The thiocyanate compound can be produced by reacting the compound shown by formula $I_{b-4}$ with a thiocyanate such as sodium thiocyanate, etc., and bromine.

The lower alkylation method (8) is a method of producing the compounds of this invention shown by formula $I_{b-1}$ wherein $R_{10}$ is a lower alkylthio group, i.e., the lower alkylthio compound shown by formula $I_{b-11}$. The lower alkylthio compound can be produced by reacting the thiocyanate compound shown by formula $I_{b-10}$ with a lower alkylating agent according to a conventional method. As the lower alkylating agent, a lower alkyl halide such as methyl iodide, ethyl iodide, etc., is used.

The compounds of this invention shown by formula I thus produced is isolated and purified by a conventional chemical operation such as concentration, recrystallization, column chromatography, etc.

Typical methods of producing the compounds of this invention shown by formula I were explained above and the compounds of this invention and the methods of producing them will be further explained more practically and in more detail by the following examples.

In addition, the results of pharmacological tests for showing the excellent pharmacological effects of the compounds of this invention shown by formula I will then be described.

Effect on adjuvant-induced arthritis in rats:

Methods: Male Sprangue Dawley rat aged 7 weeks were used. Drugs were evaluated by two methods as follows. All test drugs were suspended in water with 0.5% methylcellulose (0.5% MC) and administered orally once a day.

(1) Therapeutic effect of drugs; arthritis was induced by a single injection of 0.1 ml of sterile suspension of *Mycobacterium butyricum* (6 mg/ml) in liquid paraffin into tail skin of rats (day 0). After about 2 weeks, arthritic rats were selected and allocated into groups. Drugs were given daily following about 10 days. Thickness of the foot was measured with dial thickness gauge both on the day of initial dosing and on the next day of final dosing, change of foot thickness ($\Delta$FT $10^{-2}$ mm) was calculated as a difference between these two values. The results are shown in Table I.

(2) Prophylactic effect of drugs: arthritis was induced by single subplanter injection of 0.05 ml of the suspension into the left hind paw of rats. Drugs were given daily for 21 days starting from the day (day 0) of injection of the suspension. Thickness of both feet, injected foot (left foot, $FT_L$) and uninjected foot (right foot, $FT_R$) were measured with dial thickness gauge on day 0 and 21. The percent inhibition (I%) was calculated from difference in increased foot thickness between control and drug-treated group. The results are shown in Table II.

TABLE I

| (Therapeutic effect) | | | |
|---|---|---|---|
| Drugs | Dose (mg/kg/day P.O.) | N | Day 16– Day 17 $\Delta$ FT ($\times 10^{-2}$ mm) |
| 0.5% MC | — | 3 | 233 ± 59 |
| Indomethacin | 2 | 3 | −173 ± 62*** |
| 4-(3,5-di-tert-butyl-4-hydroxyphenyl)-5-methyl-2-oxo-4-imidazoline | 25 | 3 | −216 ± 30*** |

| Drugs | Dose (mg/kg/day P.O.) | N | Day 16– Day 25 $\Delta$ FT ($\times 10^{-2}$ mm) |
|---|---|---|---|
| 0.5% MC | — | 3 | 97 ± 91 |
| Indomethacin | 2 | 3 | −216 ± 30* |
| 4-(3,5-di-tert-butyl-4-hydroxyphenyl)-5-methyl-2-methylthioimidazole | 25 | 3 | −153 ± 56* |
| 4-(3,5-di-tert-butyl-4-hydroxyphenyl)-5-methyl-imidazole | 25 | 3 | −122 ± 46* |

| | Dose (mg/ | Day 16– |

TABLE I-continued
(Therapeutic effect)

| Drugs | kg/day P.O.) | N | Day 28 Δ FT ($10^{-2}$ mm) |
|---|---|---|---|
| 0.5% MC | — | 6 | 148 ± 37 |
| Indomethacin | 2 | 6 | −204 ± 33*** |
| 4-(3,5-di-tert-butyl-4-hydroxyphenyl)-2-mercapto-thiazole | 25 | 3 | −57 ± 26*** |
| 4-(3,5-di-tert-butyl-4-hydroxyphenyl)-2-methylthio-thiazole | 25 | 3 | −166 ± 59*** |
| 4-(3,5-di-tert-butyl-4-hydroxyphenyl)-5-ethyl-2-oxo-4-imidazoline | 25 | 3 | −247 ± 49*** |
| 4-(3,5-di-tert-butyl-4-hydroxyphenyl)-5-ethyl-imidazole | 25 | 3 | −103 ± 71** |
| 0.5% MC | — | 3 | 210 ± 91 |
| Indomethacin | 2 | 3 | −177 ± 41** |
| 6-(3,5-di-tert-butyl-4-hydroxyphenyl)-5-methyl-2,3-dihydroimidazo[2,1-b]-thiazole | 25 | 3 | −16 ± 27* |
| 6-(3,5-di-tert-butyl-4-hydroxyphenyl)-2,3-dihydro-imidazo[2,1-b]thiazole 1-oxide | 25 | 3 | −245 ± 57** |
| 6-(3,5-di-tert-butyl-4-hydroxyphenyl)-2,3-dihydro-imidazo[2,1-b]thiazole 1,1-dioxide | 25 | 3 | −141 ± 60** |

| Drugs | Dose (mg/kg/day P.O.) | N | Day 15–Day 28 Δ FT ($10^{-2}$ mm) |
|---|---|---|---|
| 0.5% MC | — | 3 | 96 ± 162 |
| Indomethacin | 2 | 3 | −161 ± 137* |
| 4-(3,5-di-tert-butyl-4-hydroxyphenyl)-5-ethyl-2-methylthio-imidazole | 25 | 3 | −180 ± 241* |

| Drugs | Dose (mg/kg/day P.O.) | N | Day 17–Day 27 Δ FT ($10^{-2}$ mm) |
|---|---|---|---|
| 0.5% MC | — | 3 | 181 ± 7 |
| Indomethacin | 2 | 3 | −225 ± 61** |
| Diclofenac HCl | 2 | 3 | −83 ± 49* |
| 6-(3,5-di-tert-butyl-4-hydroxyphenyl)-2,3-dihydro-imidazo[2,1-b]thiazole | 25 | 3 | −177 ± 36*** |

| Drugs | Dose (mg/kg/day P.O.) | N | Day 15–Day 29 Δ FT (I %) ($10^{-2}$ mm) |
|---|---|---|---|
| 0.5% MC | — | 6 | 280 ± 54 |
| Indomethacin | 1 | 6 | −243 ± 16*** (69.1) |
| | 2 | 6 | −260 ± 24*** (73.7) |
| 4-(3,5-di-tert-butyl-4-hydroxyphenyl)-5-methyl-2-oxo-4-imidazoline | 6.25 | 6 | 67 ± 48** (30.8) |
| 4-(3,5-di-tert-butyl-4-hydroxyphenyl)-5-methyl-2-oxo-4-imidazoline | 12.5 | 6 | −114 ± 33*** (53.9) |
| 4-(3,5-di-tert-butyl-4-hydroxyphenyl)-5-methyl-2-oxo-4-imidazoline | 25 | 6 | −194 ± 36*** (66.7) |
| 4-(3,5-di-tert-butyl-4-hydroxyphenyl)-5-ethyl-2-oxo-4-imidazoline | 6.25 | 6 | −19 ± 39*** (41.3) |
| 4-(3,5-di-tert-butyl-4-hydroxyphenyl)-5-ethyl-2-oxo-4-imidazoline | 12.5 | 6 | −176 ± 27*** (63.1) |
| 4-(3,5-di-tert-butyl-4-hydroxyphenyl)-5-ethyl-2-oxo-4-imidazoline | 25 | 6 | −127 ± 38*** (54.0) |

Significant difference from control (t-test)
*P < 0.05
**P < 0.01
***P < 0.001

TABLE II
(Prophylactic effect)

| Drugs | Dose (mg/kg/day P.O.) | N | Day 21 $FT_L$ 1 % | $FT_R$ 1% |
|---|---|---|---|---|
| Indomethacin | 1 | 8 | 64.6 | 81.8 |
| " | 2 | 8 | 59.5 | 76.9 |
| 4-(3,5-di-tert-butyl-4-hydroxyphenyl)-5-methyl-2-methylthioimidazole | 25 | 8 | 53.1 | 65.8 |
| 4-(3,5-di-tert-butyl-4-hydroxyphenyl)-5-methyl-imidazole | 25 | 8 | 68.1 | 81.3 |
| Indomethacin | 1 | 8 | 63.6 | 68.1 |
| " | 2 | 8 | 63.9 | 98.0 |
| 4-(3,5-di-tert-butyl-4-hydroxyphenyl)-5-methyl-2-oxo-imidazoline | 6.25 | 8 | 38.0 | 71.7 |
| 4-(3,5-di-tert-butyl-4-hydroxyphenyl)-5-methyl-2-oxo-imidazoline | 12.5 | 8 | 30.3 | 61.6 |
| 4-(3,5-di-tert-butyl-4-hydroxyphenyl)-5-methyl-2-oxo-imidazoline | 25 | 8 | 64.4 | 90.9 |
| 4-(3,5-di-tert-butyl-4-hydroxyphenyl)-5-ethyl-2-oxo-4-imidazoline | 6.25 | 8 | 11.6 | 35.8 |
| 4-(3,5-di-tert-butyl-4-hydroxyphenyl)-5-ethyl-2-oxo-4-imidazoline | 12.5 | 8 | 26.3 | 47.2 |
| 4-(3,5-di-tert-butyl-4-hydroxyphenyl)-5-ethyl-2-oxo-4-imidazoline | 25 | 8 | 60.1 | 70.1 |

As the above-described therapeutic and prohylactic test results to adjuvant-induced arthritis, it is clear that the compounds of this invention shown by formula I possess remarkable therapeutic and prohylactic effects to adjuvant-induced arthritis.

EXAMPLE 1

A mixture of 2.4 g of N-(2-phenylethyl)-thiourea, 5 g of 4-(2-bromoacetyl)-2,6-di-tert-butylphenol, and 25 ml of absolute ethanol was refluxed for 3 hours and then cooled. The precipitates thus formed were recovered by filtration and recrystallized from ethanol to provide 2.5 g of 4-(3,5-di-tert-butyl-4-hydroxyphenyl)-2-(α-phenethylamino)thiazole hydrobromide.

Melting point: 228°–230° C.

| Elemental analysis for $C_{25}H_{33}N_2OSBr$: | | | |
|---|---|---|---|
| | C (%) | H (%) | N (%) |
| Calculated: | 61.34 | 6.79 | 5.72 |
| Found: | 61.65 | 6.96 | 5.63 |

EXAMPLE 2

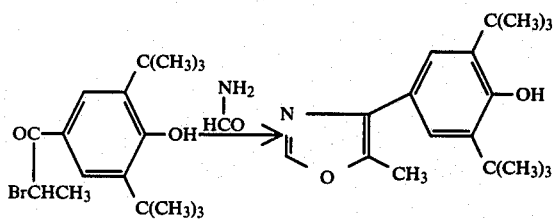

A mixture of 4.5 g of formamide and 2.25 g of 4-(2-bromopropionyl)-2,6-di-tert-butylphenol was heated to 150° C. for 1.5 hours. The reaction mixture was poured into water after cooling and then extracted twice each time with 30 ml of toluene. The extract was dried over anhydrous magnesium sulfate and concentrated under reduced pressure and the residue was recrystallized from aqueous methanol to provide 1.1 g of 4-(3,5-di-tert-butyl-4-hydroxyphenyl)-5-methyloxazole.

Melting point: 105°–107° C.

| Elemental analysis for $C_{18}H_{25}NO_2$: | | | |
|---|---|---|---|
| | C (%) | H (%) | N (%) |
| Calculated: | 75.23 | 8.77 | 4.87 |
| Found: | 75.07 | 8.91 | 4.68 |

EXAMPLE 3

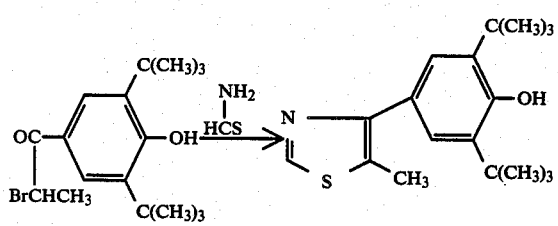

A mixture of 0.7 g of thioformamide, 3.4 g of 4-(2-bromopropionyl)-2,6-di-tert-butylphenol, and 15 ml of absolute ethanol was heated to 50°–60° C. for 2–3 hours. After cooling, the reaction mixture poured into a diluted aqueous solution of potassium carbonate. The precipitates thus formed were recovered by filtration and recrystallized from a mixture of cyclohexane and hexane to provide 1.2 g of 4-(3,5-di-tert-butyl-4-hydroxyphenyl)-5-methylthiazole.

Melting point: 128°–130° C.

| Elemental analysis for $C_{18}H_{25}NOS$: | | | |
|---|---|---|---|
| | C (%) | H (%) | N (%) |
| Calculated: | 71.24 | 8.30 | 4.62 |
| Found: | 71.39 | 8.53 | 4.38 |

EXAMPLE 4

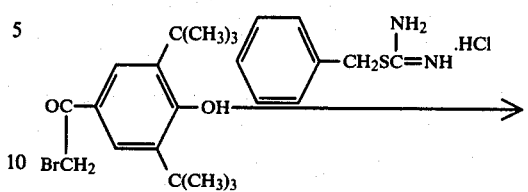

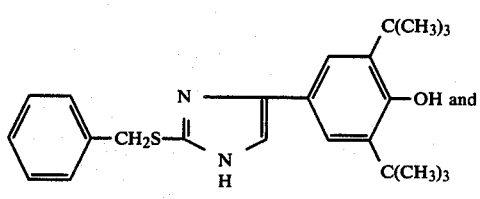

(a)

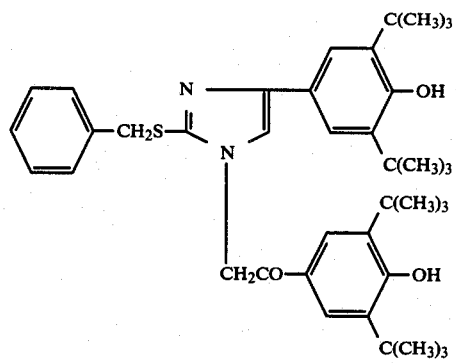

(b)

A mixture of 4 g of benzylthioformamidine hydrochloride, 6.4 g of 4-(2-bromoacetyl)-2,6-di-tert-butylphenol, 20 ml of chloroform, and 48 ml of 84% aqueous ethanol was vigorously stirred and then 6.6 g of sodium hydrogen carbonate was added to the mixture at room temperature. Thereafter, the resultant mixture was refluxed for 3 hours. The reaction mixture thus obtained was poured into water and extracted twice each time with 100 ml of benzene. The extract was dried and then concentrated under reduced pressure. The residue was subjected to silica gel column chromatography and by eluting with chloroform, two fractions were obtained. Each fraction was concentrated and recrystallized from cyclohexane to provide 1.2 g of (a) 2-benzylthio-4-(3,5-di-tert-butyl-4-hydroxyphenyl)imidazole and 0.6 g of (b) 2-benzylthio-1-(3,5-di-tert-butyl-4-hydroxyphenacyl)-4-(3,5-di-tert-butyl-4-hydroxyphenyl)imidazole respectively.

(a) Melting point: 92°–94° C.

| Elemental analysis for $C_{24}H_{30}N_2OS + \frac{1}{4} C_6H_{12}$: | | | |
|---|---|---|---|
| | C (%) | H (%) | N (%) |
| Calculated: | 74.21 | 8.25 | 6.41 |
| Found: | 73.83 | 8.43 | 6.36 |

(b) Melting point: 99°–102° C.

| Elemental analysis for $C_{40}H_{52}N_2O_3S$: | | | |
|---|---|---|---|
| | C (%) | H (%) | N (%) |
| Calculated: | 74.96 | 8.18 | 4.37 |
| Found: | 74.78 | 8.58 | 4.05 |

| Elemental analysis for $C_{24}H_{30}N_2O_2S\cdot\frac{1}{4}C_6H_{12}$: | | | |
|---|---|---|---|
| | C (%) | H (%) | N (%) |
| Found: | 71.48 | 8.16 | 6.19 |

EXAMPLE 6

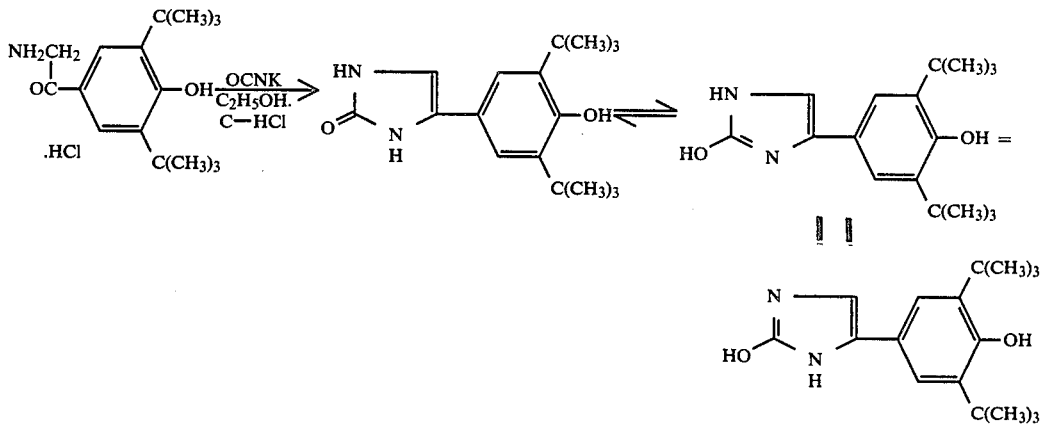

EXAMPLE 5

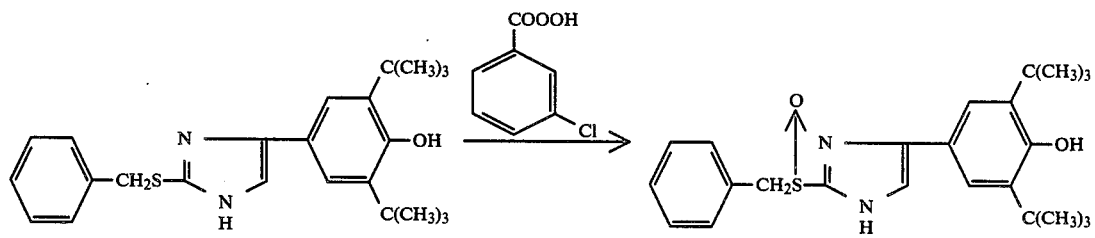

In 10 ml of chloroform was dissolved 0.8 g of 2-benzylthio-4-(3,5-di-tert-butyl-4-hydroxyphenyl)imidazole and then 0.35 g of m-chloroperbenzoic acid was added to the solution at room temperature. After the reaction was over, the reaction mixture was washed with a diluted aqueous alkali solution, dried, and concentrated under reduced pressure. The residue formed was subjected to silica gel chromatography and eluted with chloroform. The fraction thus obtained was concentrated udner reduced pressure and the residue was recrystallized from cyclohexane to provide 0.3 g of 2-benzylsulfinyl)-4-(3,5-di-tert-butyl-4-hydroxyphenyl-)imidazole.

Melting point: 189°–191° C.

| Elemental analysis for $C_{24}H_{30}N_2O_2S\cdot\frac{1}{4}C_6H_{12}$: | | | |
|---|---|---|---|
| | C (%) | H (%) | N (%) |
| Calculated: | 71.59 | 7.95 | 6.19 |

To a mixed solution of 1.2 g of 4-(2-aminoacetyl)-2,6-di-tert-butylphenol hydrochloride, 10 ml of ethanol, and 0.3 ml of concentrated hydrochloric acid was added a solution of 0.64 g of potassium isocyanate in 3 ml of water at room temperature. After stirring the mixture for 2 hours, 0.3 ml of concentrated hydrochloric acid was added thereto and the resultant mixture was refluxed for 2 hours. The reaction mixture thus obtained was poured into water and the precipitates formed were recovered by filtration. The reaction product was then recrystallized from aqueous ethanol to provide 0.5 g of 4-(3,5-di-tert-butyl-4-hydroxyphenyl)-2-oxo-4-imidazoline.

Melting point: above 260° C. (decompd.)

| Elemental analysis for $C_{17}H_{24}N_2O_2\cdot\frac{1}{4}C_2H_5OH$: | | | |
|---|---|---|---|
| | C (%) | H (%) | N (%) |
| Calculated: | 69.37 | 8.68 | 8.99 |
| Found: | 69.08 | 9.04 | 8.84 |

EXAMPLE 7

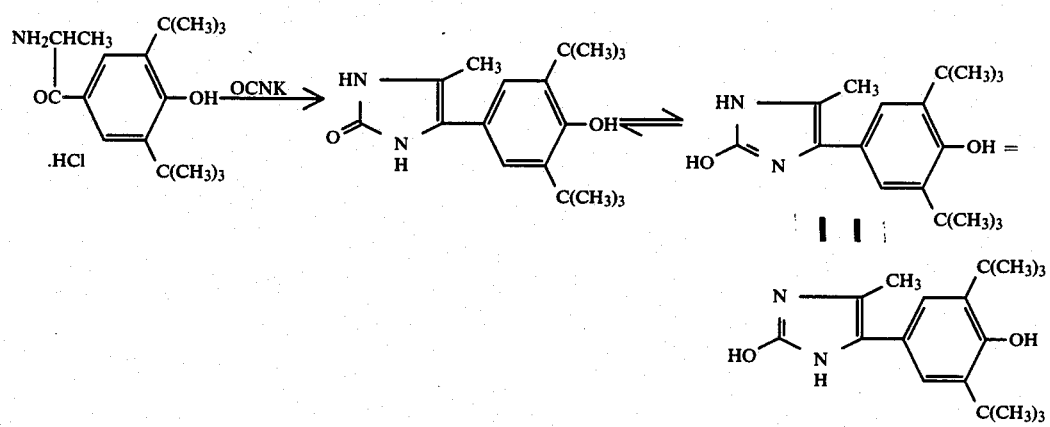

By following the same procedure as in Example 6 using 1.6 g of 4-(2-aminopropionyl)-2,6-di-tert-butyl-4-hydroxyphenol hydrochloride, 20 ml of ethanol, 0.5 ml of concentrated hydrochloric acid, 0.8 g of potassium isocyanate, a reaction product thus obtained was recrystallized from aqueous isopropanol to provide 0.7 g of 4-(3.5-di-tert-butyl-4-hydroxyphenyl)-5-methyl-2-oxo-4-imidazoline.

Melting point: above 270° C. (decompd.)

| Elemental analysis for $C_{18}H_{26}N_2O_2$: | | | |
|---|---|---|---|
| | C (%) | H (%) | N (%) |
| Calculated: | 71.49 | 8.67 | 9.26 |
| Found: | 71.47 | 8.82 | 9.22 |

This product was recrystallized from aqueous ethanol to provide the pure product having a melting point of 279°-282° C.

EXAMPLE 8

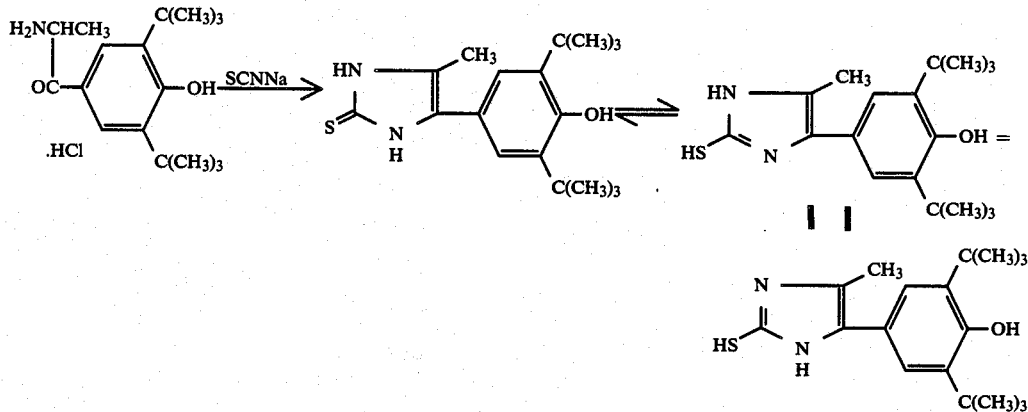

To a mixed solution of 4.3 g of 4-(2-aminopropionyl)-2,6-di-tert-butylphenol hydrochloride, 50 ml of ethanol, and 1.2 ml of concentrated hydrochloric acid was added a solution of 2.2 g of sodium thiocyanate in 4 ml of water at room temperature. After stirring the mixture for 1.5 hours at room temperature and further refluxing the mixture for 2 hours, the solvent was distilled off under reduced pressure. Then, 30 ml of acetic acid was added to the residue and the mixture was refluxed for 2-3 hours. The reaction mixture thus formed was poured into water and the precipitates formed were recovered by filtration. The product was recrysltallized from isopropanol to provide 3.1 g of 4-(3,5-di-tert-butyl-4-hydroxyphenyl)-5-methyl-2-thioxo-4-imidazoline.

Melting point: 288°-290° C.

| Elemental analysis for $C_{18}H_{26}N_2OS + (CH_3)_2CHOH$: | | | |
|---|---|---|---|
| | C (%) | H (%) | N (%) |
| Calculated: | 66.63 | 9.05 | 7.40 |
| Found: | 66.51 | 9.14 | 7.43 |

EXAMPLE 9

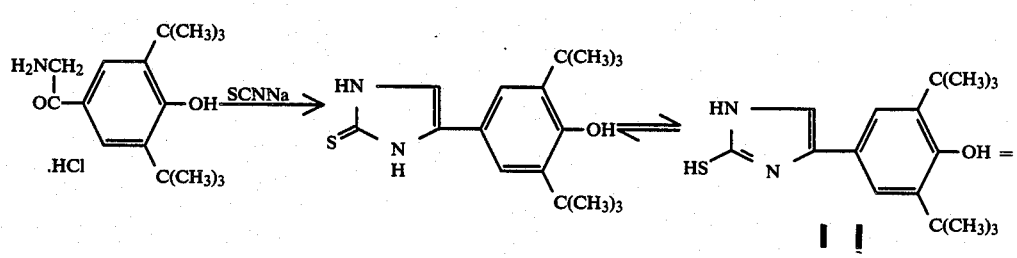

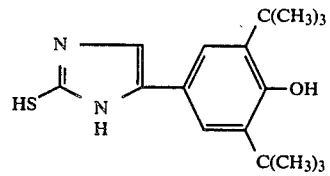

The precipitates obtained by following the same procedure as in Example 8 using 18 g of 4-(2-aminoacetyl)-2,6-di-tert-butylphenol hydrochloride, 150 ml of ethanol, and 5 ml of concentrated hydrochloric acid were subjected to silica gel chromatography and eluted with chloroform. The fraction thus obtained was concentrated under reduced pressure and the residue was recrystallized from benzenecyclohexane to provide 12 g of 4-(3,5-di-tert-butyl-4-hydroxyphenyl)-2-thioxo-4-imidazoline.

Melting point: 168°–170° C.

| Elemental analysis for $C_{17}H_{24}N_2OS + \frac{1}{2} C_6H_{12}$: | | | |
|---|---|---|---|
| | C (%) | H (%) | N (%) |
| Calculated: | 69.27 | 8.06 | 8.08 |
| Found: | 69.33 | 8.46 | 7.76 |

EXAMPLE 10

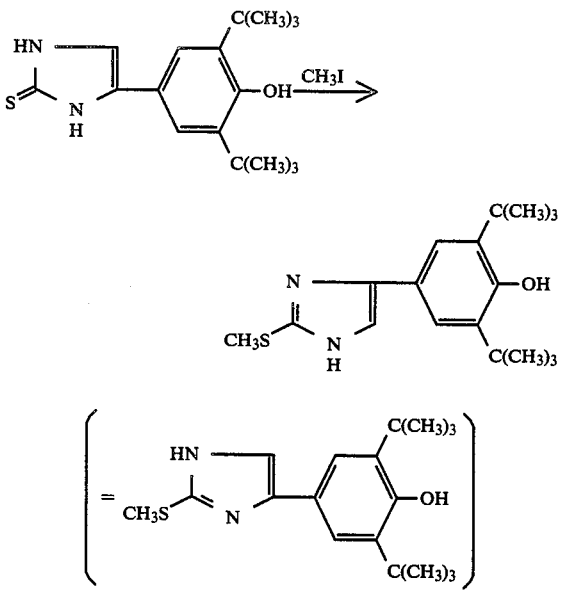

To a mixture of 3.18 g of 4-(3,5-di-tert-butyl-4-hydroxyphenyl)-2-thioxo-4-imidazoline, 50 ml of dry acetone, and 1.3 g of potassium carbonate was added 1.4 g of methyl iodide at room temperature. After stirring the mixture for one hour, the solvent was distilled off. To the residue thus formed was added water, and the precipitate formed were recovered by filtration and dried to provide 2 g of the product. Then, 0.8 g of the product was recrystallized from toluene to provide 0.5 g of 4-(3,5-di-tert-butyl-4-hydroxyphenyl)-2-methylthioimidazole.

Melting point: 249°–251° C.

| Elemental analysis for $C_{18}H_{26}N_2OS$: | | | |
|---|---|---|---|
| | C (%) | H (%) | N (%) |
| Calculated: | 67.89 | 8.23 | 8.80 |
| Found: | 67.62 | 8.36 | 8.70 |

EXAMPLE 11

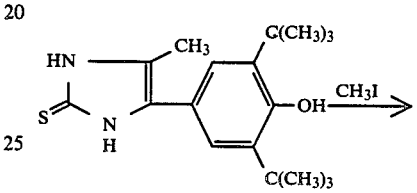

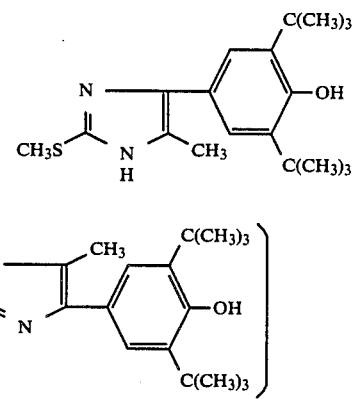

By following the same procedure as in Example 10 using 0.32 g of 4-(3,5-di-tert-butyl-4-hydroxyphenyl)-5-methyl-2-thioxo-4-imidazoline, 10 ml of dry acetone, 0.15 g of potassium carbonate, and 0.15 g of methyl iodide and recrystallizing the product from cyclohexane, 0.1 g of 4-(3,5-di-tert-butyl-4-hydroxyphenyl)-5-methyl-2-methylthioimidazole was obtained.

Melting point: 184°–186° C.

| Elemental analysis for $C_{19}H_{28}N_2OS$: | | | |
|---|---|---|---|
| | C (%) | H (%) | N (%) |
| Calculated: | 68.63 | 8.49 | 8.43 |
| Found: | 68.42 | 8.74 | 8.40 |

EXAMPLE 12

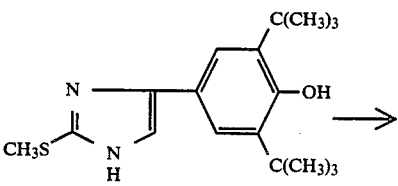

-continued

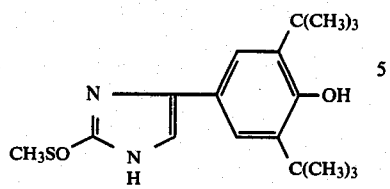

To a solution of 0.32 g of 4-(3,5-di-tert-butyl-4-hydroxyphenyl)-2-methylthioimidazole in 5 ml of chloroform was added 0.18 g of m-chloroperbenzoic acid at room temperature and the mixture was stirred for a day. The reaction mixture was washed with a diluted alkali solution, dried, concentrated under reduced pressure, and the residue thus formed was recrystallized from cyclohexane to provide 0.13 g of 4-(3,5-di-tert-butyl-4-hydroxyphenyl)-2-methylsulfinylimidazole.

Melting point: 106°–108° C.

Mass spectrum: M+ 334

Nuclear magnetic resonance spectra (in CDCl$_3$): δ(ppm): 1.48 (S; 18H), 3.1 (S; 3H); 5.3 (S; 1H), 7.32 (S; 1H), 7.44 (S; 2H).

EXAMPLE 13

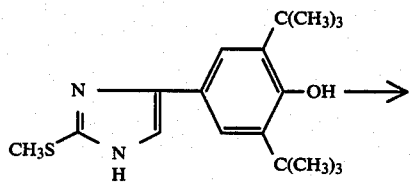

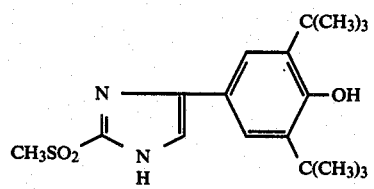

In 10 ml of 1,2-dimethoxyethane was dissolved 0.62 g of 4-(3,5-di-tert-butyl-4-hydroxyphenyl)-2-methylthioimidazole and after adding thereto 0.44 g of m-chloroperbenzoic acid, the mixture was refluxed for 3–4 hours. The reaction mixture was cooled, washed with a diluted alkali solution, dried, and concentrated under reduced pressure. The residue thus formed was recrystallized from cyclohexane to provide 0.5 g of 4-(3,5-di-tert-butyl-4-hydroxyphenyl)-2-methylsulfonylimidazole.

Melting point: 119°–120° C.

Mass spectrum: M+ 350

Nuclear magnetic resonance spectra (in CDCl$_3$): δ(ppm): 1.4 (S, 18H), 3.06 (S, 3H), 5.06 (S, 1H), 7.3 (S, 1H), 7.3 (S, 1H), 7.48 (S, 2H). EXAMPLE 14

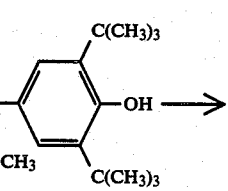

-continued

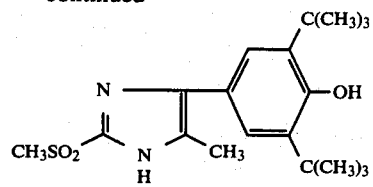

By following the same procedure as in Example 13 using 0.9 g of 4-(3,5-di-tert-butyl-4-hydroxyphenyl)-5-methyl-2-methylthioimidazole, 10 ml of 1,2-dimethoxyethane, and 0.64 g of m-chloroperbenzoic acid and recrystallizing the product from toluene, 0.3 g of 4-(3,5-di-tert-butyl-4-hydroxyphenyl)-5-methyl-2-methylsulfonylimidazole was obtained.

Melting point: 235°–237° C.

| Elemental analysis for C$_{19}$H$_{28}$N$_2$O$_3$S: | | | |
|---|---|---|---|
| | C (%) | H (%) | N (%) |
| Calculated: | 62.61 | 7.74 | 7.69 |
| Found: | 62.91 | 8.01 | 7.25 |

EXAMPLE 15

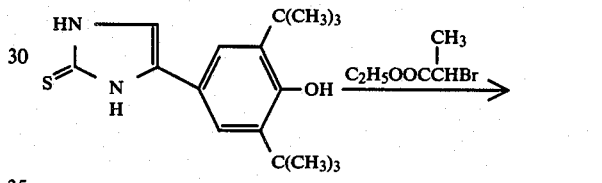

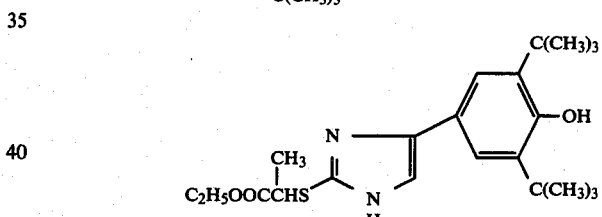

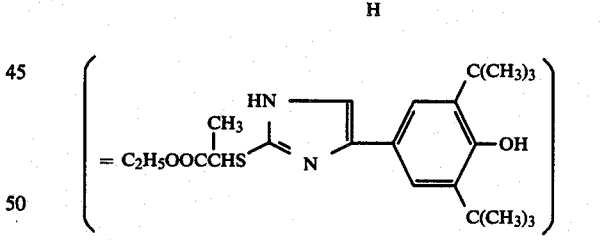

By following the same procedure as in Example 10 using 1.8 g of 4-(3,5-di-tert-butyl-4-hydroxyphenyl)-2-thioxo-4-imidazoline, 30 ml of dry acetone, 0.99 g of potassium carbonate, and 1.3 g of ethyl α-bromopropionate and recrystallizing the product from a mixture of toluene and cyclohexane, 0.95 g of ethyl 2-[4-(3,5-di-tert-butyl-4-hydroxyphenyl)-2-imidazolylthio]propionate was obtained.

Melting point: 80°–82° C.

| Elemental analysis for C$_{22}$H$_{32}$N$_2$O$_3$S: | | | |
|---|---|---|---|
| | C (%) | H (%) | N (%) |
| Calculated: | 65.31 | 7.97 | 6.92 |
| Found: | 65.58 | 8.19 | 6.63 |

EXAMPLE 16

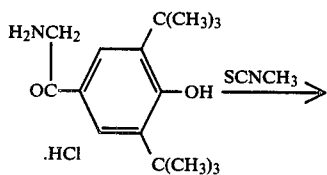

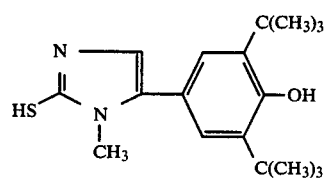

After stirring a mixture of 100 ml of pyridine, 6 g of methyl isothiocyanate, and 3 g of 4-(2-aminoacetyl)-2,6-di-tert-butylphenol hydrochloride at room temperature for 2 hours, the resulted mixture was maintained at an inside temperature of 80°–90° C. for 1.5 hours. The reaction mixture was concentrated udner reduced pressure and then the residue was extracted with 100 ml of ethyl acetate. The extract was washed with diluted hydrochloric acid, dried, and concentrated under reduced pressure. The residue was recrystallized from ethanol to provide 0.6 g of 5-(3,5-di-tert-butyl-4-hydroxyphenyl)-2-mercapto-1-methylimidazole.

Melting point: 288°–289° C.

Nuclear magnetic resonance spectra (in CDCl₃): δ(ppm): 1.44 (S, 18H), 3.54 (S, 3H), 5,38 (S, 1H), 6,64 (S, 1H), 7.08 (S, 2H).

Mass spectrum: M+ 318

EXAMPLE 17

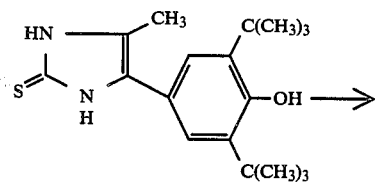

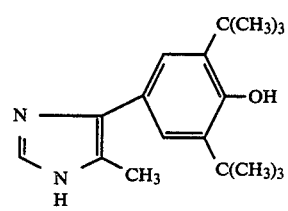

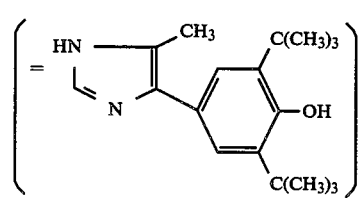

A mixture of 1.5 g of 4-(3,5-di-tert-butyl-4-hydroxyphenyl)-5-methyl-2-thioxo-4-imidazoline, 0.5 g of a Raney nickel catalyst, and 50 ml of absolute ethanol was refluxed for one hour and after filtering the reaction mixture, the filtrate was concentrated under reduced pressure. The residue was recrystallized from a mixture of cyclohexane and n-hexane to provide 1 g of 4-(3,5-di-tert-butyl-4-hydroxyphenyl)-5-methylimidazole.

Melting point: 207°–209° C.

| Elemental Analysis for C₁₈H₂₆N₂O: | | | |
|---|---|---|---|
| | C (%) | H (%) | N (%) |
| Calculated: | 75.48 | 9.15 | 9.78 |
| Found: | 75.31 | 9.40 | 9.53 |

EXAMPLE 18

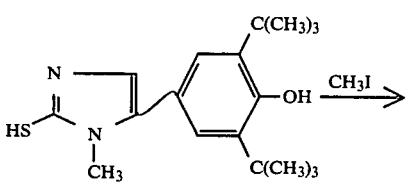

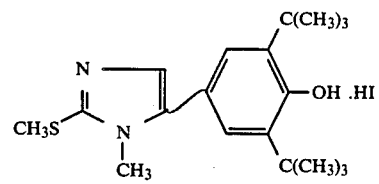

To a solution of 0.6 g of potassium hydroxide dissolved in 10 ml of ethanol was added 1.6 g of 4-(3,5-di-tert-butyl-4-hydroxyphenyl)-2-mercapto-1-methylimidazole at a temperature below 10° C. and the mixture was stirred for 20 minutes. Thereafter, 0.7 g of methyl iodide was added to the mixture and after further stirring the mixture for 3 hours at 10° C., the resulted mixture was poured into diluted hydrochloric acid and extracted twice each time with 50 ml of ethyl acetate. The extract was dried, concentrated under reduced pressure, and then the residue was recrystallized from isopropanol to provide 0.75 g of 5-(3,5-di-tert-butyl-4-hydroxyphenyl)-1-methyl-2-methylthioimidazole hydroiodide.

Melting point: 215°–217° C.

| Elemental analysis for C₁₉H₂₉N₂OSI: | | | |
|---|---|---|---|
| | C (%) | H (%) | N (%) |
| Calculated: | 49.57 | 6.30 | 6.08 |
| Found: | 49.48 | 6.33 | 5.96 |

Mass spectrum: M+ 332

EXAMPLE 19

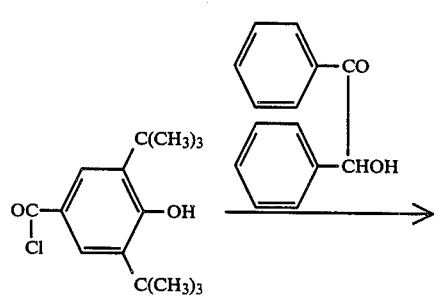

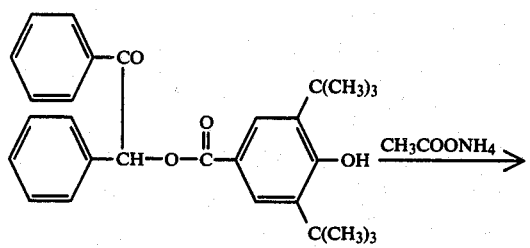

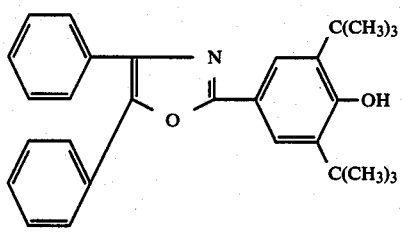

In 10 ml of pyridine was dissolved 2.1 g of benzoin and after adding thereto 2.7 g of 3,5-di-tert-butyl-4-hydroxybenzoyl chloride, the mixture was stirred for 15 hours. The reaction mixture was poured into water and extracted with ethyl acetate. The extract was washed with diluted hydrochloric acid, dried, and then the solvent was distilled off. The crystals thus formed were purified by silica gel column chromatography using chloroform as the eluent to provide 1.7 g of 3,5-di-tert-butyl-4-hydroxybenzoic acid benzoin ester. Then, 1.5 g of the ester was dissolved in 25 ml of acetic acid and after adding 3 g of ammonium acetate to the solution, the mixture was refluxed for one hour. To the reaction mixture was added 20 ml of water and the crystals thus precipitated wre recovered by filtration and recrystallized from ethanol to provide 1.0 g of 2-(3,5-di-tert-butyl-4-hydroxyphenyl)-4,5-diphenyloxazole.

Melting point: 185°–186° C.

| Elemental analysis for C$_{29}$H$_{31}$NO$_2$: | | | |
|---|---|---|---|
| | C (%) | H (%) | N (%) |
| Calculated: | 81.85 | 7.34 | 3.29 |
| Found: | 81.64 | 7.58 | 3.24 |

EXAMPLE 20

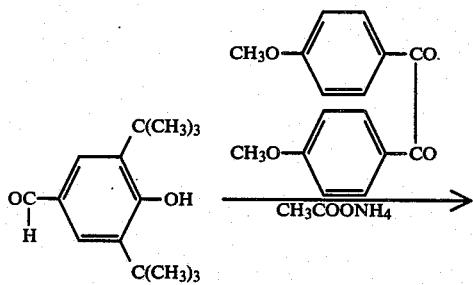

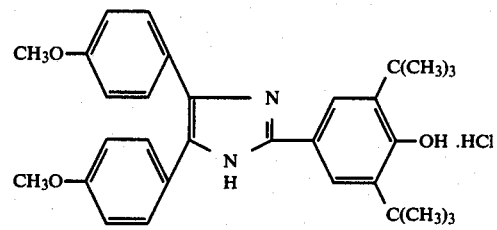

In 20 ml of acetic acid was dissolved 1.4 g of p-anisil after adding thereto 1.2 g of 3,5-di-tert-butyl-4-hydroxybenzaldehyde and 5 g of ammonium acetate, the mixture was refluxed for one hour. To the reaction mixture was added 10 ml of water and the crystals thus precipitated were recovered by filtration and dissolved in 30 ml of chloroform. After washing the chloroform solution with diluted aqueous ammonia, the solvent was distilled off. The crystals thus obtained were washed with water and then methanol, treated with hydrogen chloride-containing methanol, and recrystallized from a mixture of methanol and ether to provide 1.4 g of 2-(3,5-di-tert-butyl-4-hydroxyphenyl)-4,5-bis(p-methoxyphenyl)imidazole hydrochloride.

Melting point: 292°–295° C.

| Elemental Analysis for C$_{31}$H$_{37}$N$_2$O$_3$Cl: | | | |
|---|---|---|---|
| | C (%) | H (%) | N (%) |
| Calculated: | 71.45 | 7.16 | 5.35 |
| Found: | 71.08 | 7.23 | 5.38 |

EXAMPLE 21

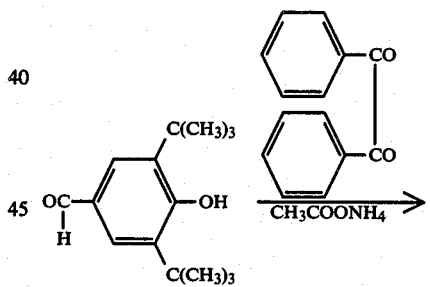

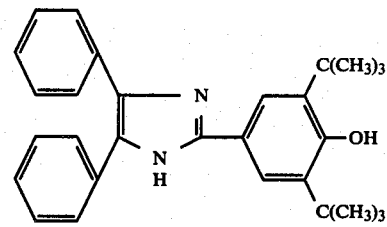

By following the same procedure as in Example 20 using 1.05 g of benzil, 1.8 g of 2-(3,5-di-tert-butyl-4-hydroxyphenyl)-4,5-diphenylimidazole hydrochloride was obtained.

Melting point: above 300° C.

| Elemental analysis for C$_{29}$H$_{33}$N$_2$OCl: | | | |
|---|---|---|---|
| | C (%) | H (%) | N (%) |
| Calculated: | 75.55 | 7.21 | 6.08 |

-continued

Elemental analysis for $C_{29}H_{33}N_2OCl$:

| | C (%) | H (%) | N (%) |
|---|---|---|---|
| Found: | 75.38 | 7.32 | 6.07 |

EXAMPLE 22

In 60 ml of ethanol was suspended 10 g of ammonium amidodithiocarbonate and 15 g of α-bromo-3,5-di-tert-butyl-4-hydroxyacetophenone was added portionwise to the suspension under stirring at 0°–5° C. Then, after stirring the mixture overnight at room temperature, 200 ml of water was added to the reaction mixture and the product was extracted with benzene. The extract was concentrated and the residue was dissolved in 50 ml of acetic acid and refluxed for 4 hours. To the reaction mixture were added 150 ml of water and 50 ml of ethyl acetate and then the mixture was stirred. The crystals thus precipitated were recovered by filtration and recrystallized from dioxane to provide 9.5 g of 4-(3,5-di-tert-butyl-4-hydroxyphenyl)-2-mercaptothiazole as the ½ dioxane addition product thereof.

Melting point: 285°–288° C.

Elemental analysis for $C_{19}H_{27}O\ NS_2$:

| | C (%) | H (%) | N (%) |
|---|---|---|---|
| Calculated: | 62.43 | 7.44 | 3.83 |
| Found: | 62.31 | 7.47 | 3.96 |

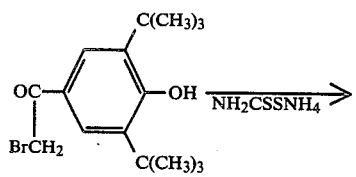

EXAMPLE 23

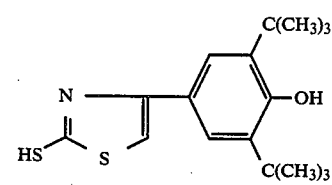

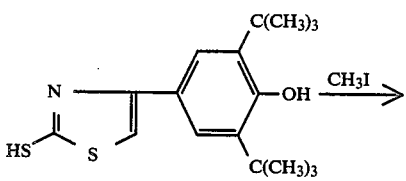

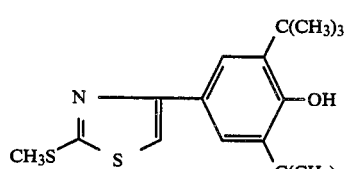

In 30 ml of methanol was dissolved 0.18 g of metallic sodium and after adding thereto 2.1 g of 4-(3,5-di-tert-butyl-4-hydroxyphenyl)-2-mercaptothiazole, 1.15 g of methyl iodide was added dropwise to the solution at 0°–5° C. After allowing to stand the mixture for 30 minutes at room temperature, 60 ml of iced water was added to the reaction mixture. The crystals thus precipitated were recovered by filtration and recrystallized from n-hexane to provide 1.6 g of 4-(3,5-di-tert-butyl-4-hydroxyphenyl)-2-methylthiothiazole.

Melting point: 92°–93° C.

Elemental analysis for $C_{18}H_{25}NOS_2$:

| | C (%) | H (%) | N (%) | S (%) |
|---|---|---|---|---|
| Calculated: | 64.44 | 7.51 | 4.17 | 19.11 |
| Found: | 64.36 | 7.69 | 4.23 | 19.28 |

EXAMPLE 24

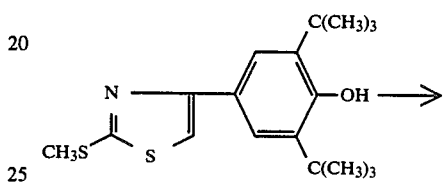

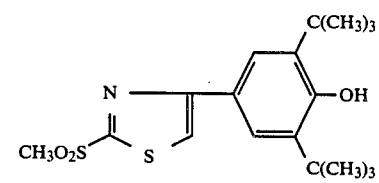

In 30 ml of chloroform was dissolved 0.8 g of 4-(3,5-di-tert-butyl-4-hydroxyphenyl)-2-methylthiothiazole and then 1.5 g of m-chloroperbenzoic acid was added portionwise to the solution with stirring. After one hour, the reaction mixture was washed with a 5% sodium hydrogen carbonate solution, and the chloroform layer was concentrated. The crystals obtained were recrystallized from methanol to provide 0.55 g of 3,5-di-tert-butyl-4-hydroxyphenyl-2-methylsulfonylthiazole.

Melting point: 183°–184° C.

Elemental analysis for $C_{18}H_{25}NO_3S_2$:

| | C (%) | H (%) | N (%) | S (%) |
|---|---|---|---|---|
| Calculated: | 58.83 | 6.86 | 3.81 | 17.45 |
| Found: | 58.72 | 7.00 | 3.69 | 17.66 |

EXAMPLE 25

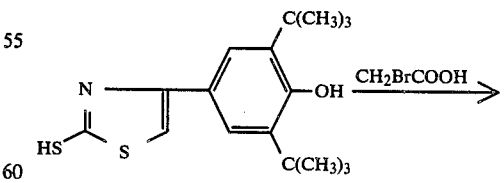

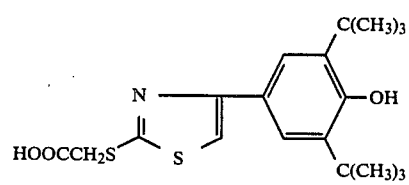

To 20 ml of benzene were added 0.64 g of 4-(3,5-di-tert-butyl-4-hydroxyphenyl)-2-mercaptothiazole and 0.32 g of bromoacetic acid and then 0.5 g of triethylamine was added dropwise to the mixture with stirring. After one hour, triethylamine hydrobromide thus precipitated was filtered off and the benzene solution was extracted with 10 ml of a 2% sodium hydroxide solution. The aqueous extract was acidified by the addition of hydrochloric acid and extracted with ether. The ether solution was dried over anhydrous sodium sulfate and concentrated. The crystals thus obtained were recrystallized from benzene to provide 0.52 g of [4-(3,5-di-tert-butyl-4-hydroxyphenyl)-2-thiazolylthio]acetic acid.

Melting point: 158°–159° C.

| Elemental analysis for $C_{19}H_{25}NO_3S_2$: | | | | |
|---|---|---|---|---|
| | C (%) | H (%) | N (%) | S (%) |
| Calculated: | 60.13 | 6.64 | 3.69 | 16.89 |
| Found: | 60.06 | 6.62 | 3.77 | 16.69 |

EXAMPLE 26

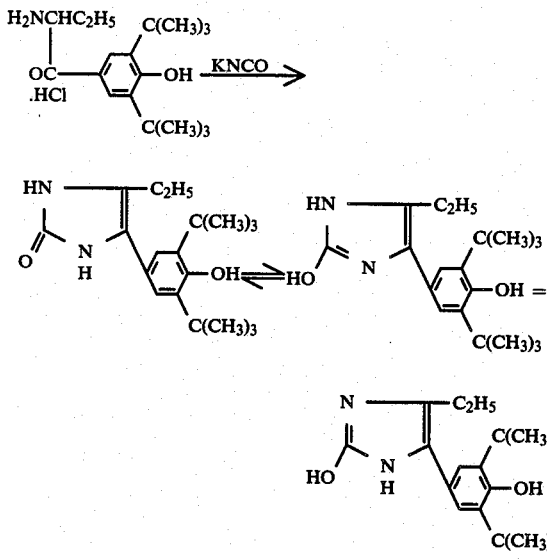

By following the same procedure as in Example 6 using 3.3 g of 2-amino-1-(3,5-di-tert-butyl-4-hydroxyphenyl)-1-butanone hydrochloride, 1.62 g of potassium isocyanate, and 1.6 ml of concentrated hydrochloric acid and recrystallizing the reaction product from aqueous isopropanol, 1.6 g of 4-(3,5-di-tert-butyl-4-hydroxyphenyl)-5-ethyl-2-oxo-4-imidazoline was obtained.

Melting point: 267°–270° C.

| Elemental analysis for $C_{19}H_{28}N_2O_2$: | | | |
|---|---|---|---|
| | C (%) | H (%) | N (%) |
| Calculated: | 72.12 | 8.92 | 8.85 |
| Found: | 71.83 | 9.17 | 8.62 |

EXAMPLE 27

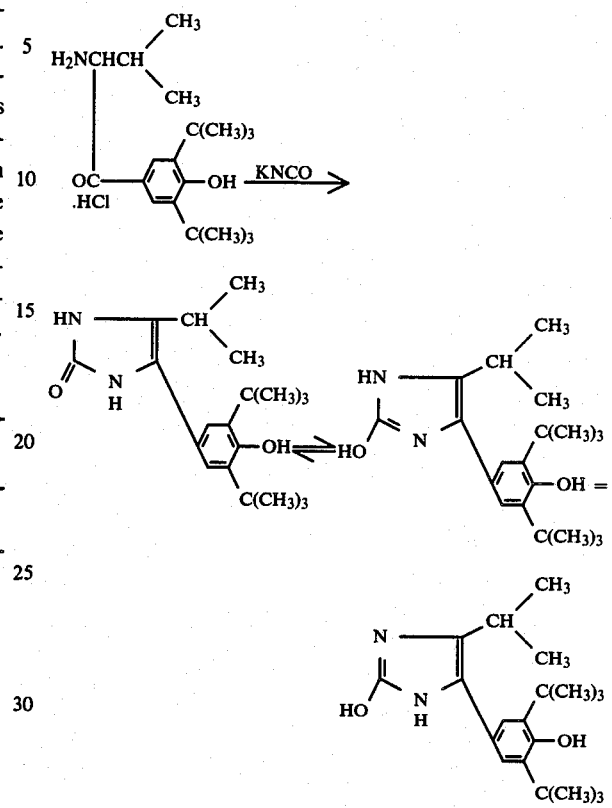

By following the same procedure as in Example 6 using 1.7 g of 2-amino-1-(3,5-di-tert-butyl-4-hydroxyphenyl)-3-methyl-1-butanone hydrochloride, 0.8 g of potassium isocyanate, and 1 ml of concentrated hydrochloric acid and recrystallizing the reaction product from aqueous isopropanol, 0.35 g of 4-(3,5-di-tert-butyl-4-hydroxyphenyl)-5-isopropyl-2-oxo-4-imidazoline was obtained.

Melting point: above 290° C. (decompd.)

| Elemental analysis for $C_{20}H_{30}N_2O_2$: | | | |
|---|---|---|---|
| | C (%) | H (%) | N (%) |
| Calculated: | 72.69 | 9.15 | 8.48 |
| Found: | 72.37 | 9.26 | 8.47 |

EXAMPLE 28

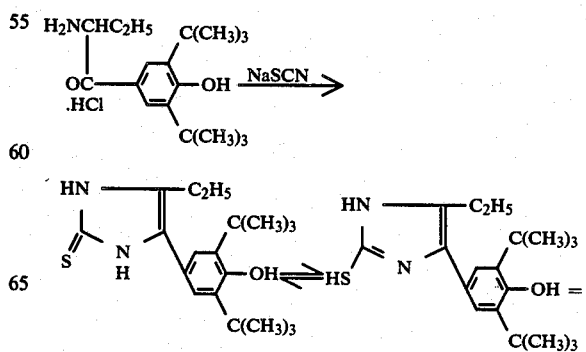

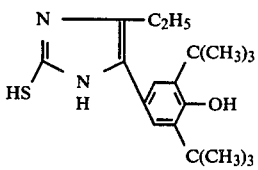

By following the same procedure as in Example 8 using 13.1 g of 2-amino-1-(3,5-di-tert-butyl-4-hydroxyphenyl)-1-butanone hydrochloride, 6.5 g of sodium thiocyanate, 3.4 ml of concentrated, and 100 ml of acetic acid and recrystallizing the reaction product from isopropanol, 6 g of 4-(3,5-di-tert-butyl-4-hydroxyphenyl)-5-ethyl-2-thioxo-4-imidazoline was obtained.

Melting point: 279°–281° C.

| Elemental analysis for $C_{19}H_{28}N_2OS + (CH_3)_2CHOH$: | | | |
|---|---|---|---|
| | C (%) | H (%) | N (%) |
| Calculated: | 67.31 | 9.24 | 7.14 |
| Found: | 67.17 | 9.36 | 7.29 |

EXAMPLE 29

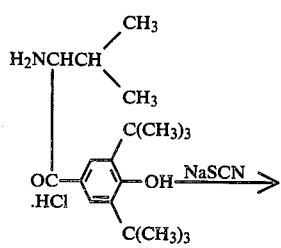

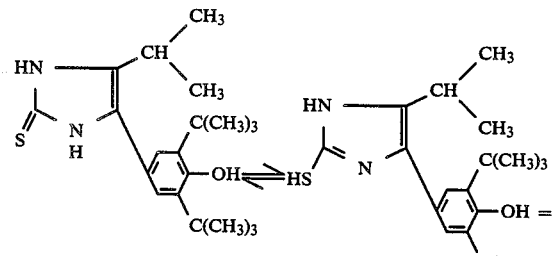

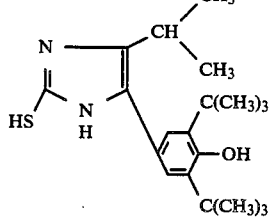

By following the same procedure as in Example 8 using 3.4 g of 2-amino-1-(3,5-di-tert-butyl-4-hydroxyphenyl)-3-methyl-1-butanone hydrochloride, 1.6 g of sodium thiocyanate, 1 ml of concentrated hydrochloric acid, and 31 ml of acetic acid and recrystallizing the reaction product from water-containing isopropanol, 0.8 g of 4-(3,5-di-tert-butyl-4-hydroxyphenyl)-5-isopropyl-2-thioxo-4-imidazoline was obtained.

Melting point: above 300° C. (decomp.)

| Elemental analysis for $C_{20}H_{30}N_2OS$: | | | |
|---|---|---|---|
| | C (%) | H (%) | N (%) |
| Calculated: | 69.32 | 8.73 | 8.08 |
| Found: | 69.18 | 8.95 | 7.74 |

EXAMPLE 30

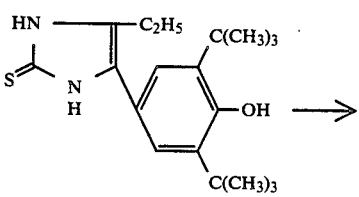

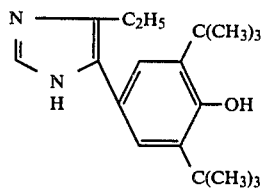

By following the same procedure as in Example 17 using 2 g of 4-(3,5-di-tert-butyl-4-hydroxyphenyl)-5-ethyl-2-thioxo-4-imidazoline, 50 ml of absolute ethanol, and 1 g of a Raney nickel catalyst and recrystallizing the reaction product from toluene, 0.9 g of 4-(3,5-di-tert-butyl-4-hydroxyphenyl)-5-ethylimidazole was obtained.

Melting point: 200°–201° C.

| Elemental analysis for $C_{19}H_{28}N_2O + \frac{1}{4} C_7H_8$: | | | |
|---|---|---|---|
| | C (%) | H (%) | N (%) |
| Calculated: | 77.99 | 9.31 | 8.08 |
| Found: | 77.72 | 9.53 | 8.13 |

EXAMPLE 31

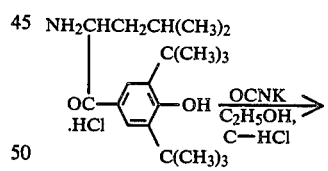

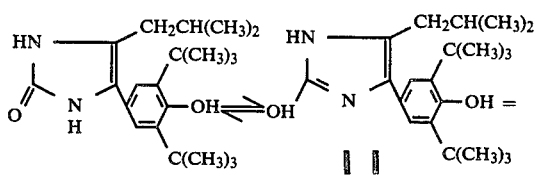

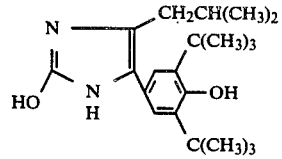

By following the same procedure as in Example 6, 4-(3,5-di-tert-butyl-4-hydroxyphenyl)-5-isobutyl-2-oxo-4-imidazoline was produced.

Melting point: 286°–289° C. (benzene-hexane)

| Elemental analysis for $C_{21}H_{32}N_2O_2$: | | | |
|---|---|---|---|
| | C (%) | H (%) | N (%) |
| Calculated: | 73.22 | 9.36 | 8.13 |
| Found: | 73.43 | 9.57 | 8.18 |

EXAMPLES 32–38

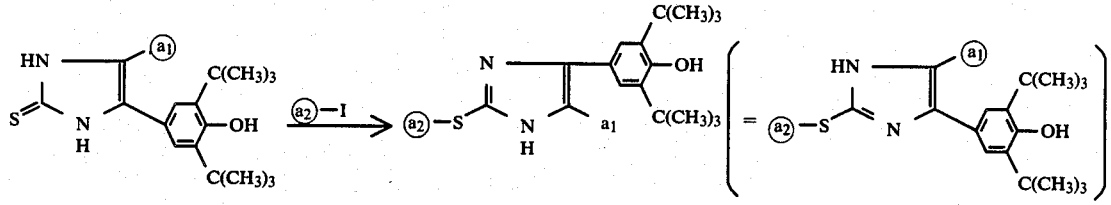

By following the same procedure as in Example 10, the following compounds were produced.

EXAMPLE 32

Compound: 4-(3,5-di-tert-butyl-4-hydroxyphenyl)-2-ethylthio-5-methylimidazole. ($a_1$ =CH$_3$, $a_2$ =CH$_2$CH$_3$)
Melting point: 245°–250° C. (toluene)

| Elemental analysis for $C_{20}H_{30}N_2OS$: | | | | |
|---|---|---|---|---|
| | C (%) | H (%) | N (%) | S (%) |
| Calculated: | 69.32 | 8.73 | 8.08 | 9.25 |
| Found: | 69.38 | 8.70 | 8.00 | 9.47 |

EXAMPLE 33

Compound: 4-(3,5-di-tert-butyl-4-hydroxyphenyl)-2-isopropylthio-5-methylimidazole.

($a_1$ = CH$_3$, $a_2$ = CH(CH$_3$)$_2$)

Melting point: 250°–258° C. (toluene)

| Elemental analysis for $C_{21}H_{32}N_2OS$: | | | | |
|---|---|---|---|---|
| | C (%) | H (%) | N (%) | S (%) |
| Calculated: | 69.96 | 8.95 | 7.77 | 8.89 |
| Found: | 69.74 | 9.02 | 7.61 | 8.63 |

EXAMPLE 34

Compound: 4-(3,5-di-tert-butyl-4-hydroxyphenyl)-5-ethyl-2-methylthioimidazole. ($a_1$ =CH$_2$CH$_3$, $a_2$ =CH$_3$)
Melting point: 210°–211° C. (toluene)

| Elemental analysis for $C_{20}H_{30}N_2OS$: | | | |
|---|---|---|---|
| | C (%) | H (%) | N (%) |
| Calculated: | 69.32 | 8.73 | 8.08 |
| Found: | 69.05 | 8.68 | 7.48 |

EXAMPLE 35

Compound: 4-(3,5-di-tert-butyl-4-hydroxyphenyl)-5-ethyl-2-ethylthioimidazole. ($a_1$ =CH$_2$CH$_3$, $a_2$ =CH$_2$CH$_3$)
Melting point: 226°–228° C. (toluene)

| Elemental analysis for $C_{21}H_{32}N_2OS$: | | | |
|---|---|---|---|
| | C (%) | H (%) | N (%) |
| Calculated: | 69.96 | 8.95 | 7.74 |
| Found: | 70.18 | 8.97 | 7.63 |

EXAMPLE 36

Compound: 4-(3,5-di-tert-butyl-4-hydroxyphenyl)-5-ethyl-2-isopropylthioimidazole.

($a_1$ = CH$_2$CH$_3$, $a_2$ = CH(CH$_3$)$_2$)

Melting point: 247°–248° C. (toluene)

| Elemental analysis for $C_{22}H_{34}N_2OS$: | | | |
|---|---|---|---|
| | C (%) | H (%) | N (%) |
| Calculated: | 70.54 | 9.15 | 7.48 |
| Found: | 70.32 | 9.27 | 7.37 |

EXAMPLE 37

Compound: 4-(3,5-di-tert-butyl-4-hydroxyphenyl)-5-isopropyl-2-methylthioimidazole.

($a_1$ = CH(CH$_3$)$_2$, $a_2$ = CH$_3$)

Melting point: 222°–223° C. (ethyl acetate hexane)

| Elemental analysis for $C_{21}H_{32}N_2OS$: | | | |
|---|---|---|---|
| | C (%) | H (%) | N (%) |
| Calculated: | 69.96 | 8.95 | 7.77 |
| Found: | 69.78 | 9.01 | 7.65 |

EXAMPLE 38

Compound: 4-(3,5-di-tert-butyl-4-hydroxyphenyl)-5-isobutyl-2-methylthioimidazole.

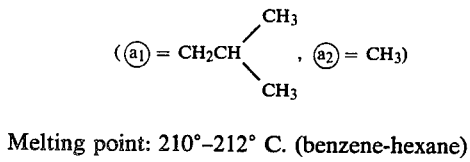

Melting point: 210°–212° C. (benzene-hexane)

| Elemental analysis for $C_{22}H_{34}N_2OS$: | | | |
|---|---|---|---|
| | C (%) | H (%) | N (%) |
| Calculated: | 70.54 | 9.15 | 7.48 |
| Found: | 70.45 | 9.24 | 7.07 |

EXAMPLE 39

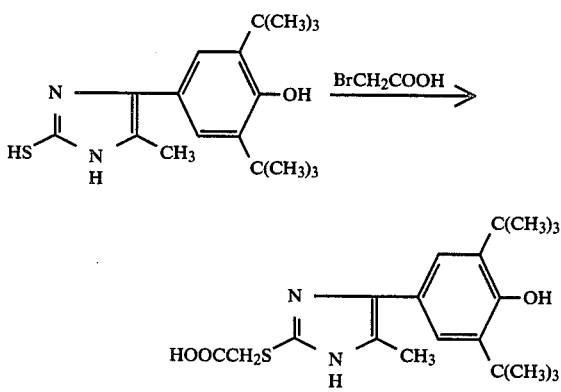

In 30 ml of toluene were dissolved 1.6 g of 4-(3,5-di-tert-butyl-4-hydroxyphenyl)-5-methyl-2-thioxo-4-imidazoline and 0.7 g of bromoacetic acid and after adding thereto 1 g of triethylamine at room temperature, the mixture was refluxed for 4 hours. After cooling, the reaction mixture was filtrated and the filtrate was extracted with an aqueous sodium carbonate solution and the alkali solution was acidified with diluted hydrochloric acid. The precipitates thus formed were recovered by filtration and recrystallized from aqueous isopropanol to provide 0.5 g of [4-(3,5-di-tert-butyl-4-hydroxyphenyl)-5-methyl-2-imidazoylthio]acetic acid.
Melting point: 252°–254° C.

| Elemental analysis for $C_{20}H_{28}N_2O_3S$: | | | |
|---|---|---|---|
| | C (%) | H (%) | N (%) |
| Calculated: | 63.80 | 7.50 | 7.44 |
| Found: | 63.53 | 7.74 | 7.26 |

EXAMPLE 40

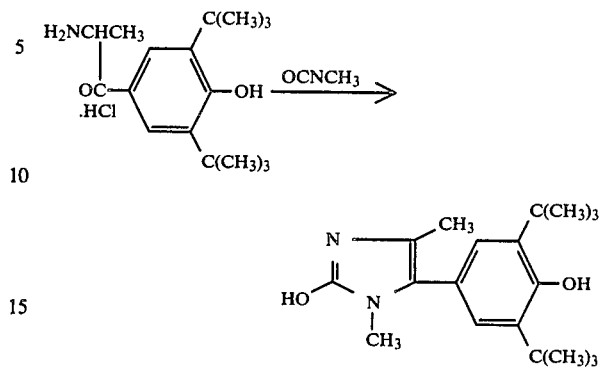

By following the same procedure as in Example 16, 5-(3,5-di-tert-butyl-4-hydroxyphenyl)-1,4-dimethyl-2-oxo-4-imidazoline was produced.
Melting point: 285°–286° C.

| Elemental analysis for $C_{19}H_{28}N_2O_2$: | | | |
|---|---|---|---|
| | C (%) | H (%) | N (%) |
| Calculated: | 72.12 | 8.92 | 8.85 |
| Found: | 72.18 | 9.18 | 8.57 |

EXAMPLES 41–42

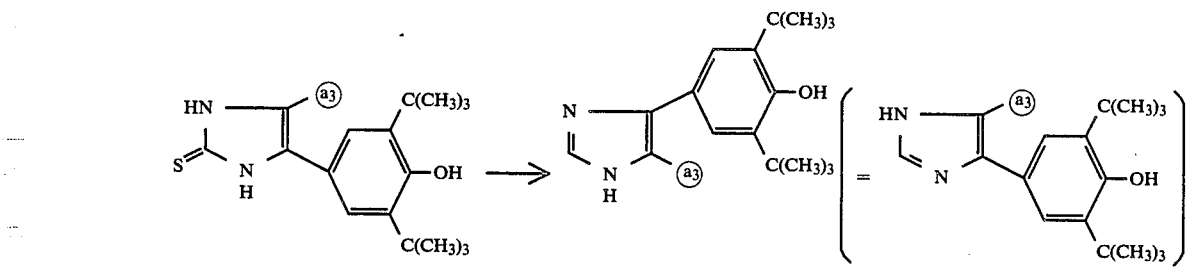

By following the same procedure as in Example 17, the following compounds were produced.

EXAMPLE 41

Compound: 4-(3,5-di-tert-butyl-4-hydroxyphenyl)-5-isopropylimidazole.½CH₃OH

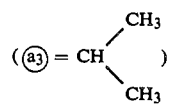

Melting point: 208°–210° C. (methanol)

| Elemental analysis for $C_{20}H_{30}N_2O.\frac{1}{2}CH_3OH$: | | | |
|---|---|---|---|
| | C (%) | H (%) | N (%) |
| Calculated: | 74.50 | 9.76 | 8.48 |
| Found: | 74.23 | 10.08 | 8.43 |

EXAMPLE 42

Compound: 4-(3,5-di-tert-butyl-4-hydroxyphenyl)-5-isobutylimidazole.

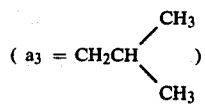

Melting point: 202°–203° C. (benzene)

| | Elemental analysis for $C_{21}H_{32}N_2O$: | | |
|---|---|---|---|
| | C (%) | H (%) | N (%) |
| Calculated: | 76.78 | 9.82 | 8.53 |
| Found: | 76.64 | 9.95 | 8.45 |

EXAMPLE 43

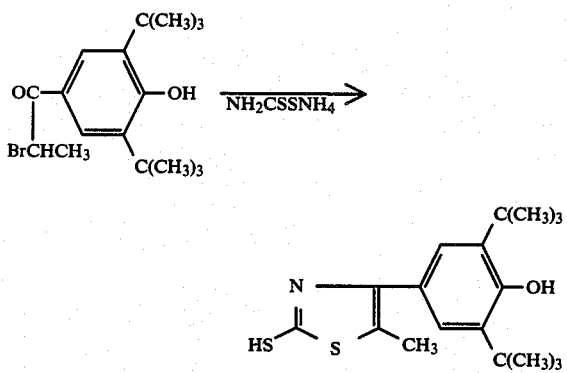

By following the same procedure as in Example 22, 4-(3,5-di-tert-butyl-4-hydroxyphenyl)-2-mercapto-5-methylthiazole was produced.

Melting point: 267°–269° C. (tetrahydrofuran-hexane)

| | Elemental analysis for $C_{18}H_{25}NOS_2$: | | |
|---|---|---|---|
| | C (%) | H (%) | N (%) |
| Calculated: | 64.44 | 7.51 | 4.17 |
| Found: | 64.29 | 7.50 | 4.16 |

EXAMPLE 44–49

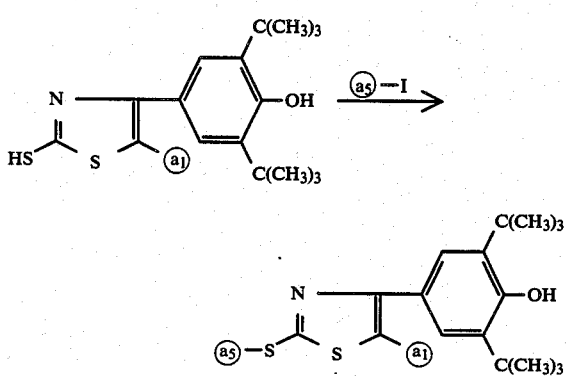

By following the same procedure as in Example 23, the following compounds were produced.

EXAMPLE 44

Compound: 4-(3,5-di-tert-butyl-4-hydroxyphenyl)-2-ethylthiothiazole. ( $a_4$ =H, $a_5$ =CH$_2$CH$_3$)

Melting point: 130°–131° C. (methanol)

| | Elemental analysis for $C_{19}H_{27}NOS_2$: | | | |
|---|---|---|---|---|
| | C (%) | H (%) | N (%) | S (%) |
| Calculated: | 65.29 | 7.79 | 4.01 | 18.34 |
| Found: | 64.97 | 7.99 | 4.01 | 18.38 |

EXAMPLE 45

Compound: 4-(3,5-di-tert-butyl-4-hydroxyphenyl)-2-isopropylthiothiazole.

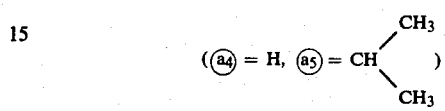

Melting point: 173°–174° C. (hexane)

| | Elemental analysis for $C_{20}H_{29}NOS_2$: | | | |
|---|---|---|---|---|
| | C (%) | H (%) | N (%) | S (%) |
| Calculated: | 66.07 | 8.04 | 3.85 | 17.64 |
| Found: | 66.20 | 7.84 | 3.67 | 17.80 |

EXAMPLE 46

Compound: 4-(3,5-di-tert-butyl-4-hydroxyphenyl)-5-methyl-2-methylthiothiazole. ( $a_4$ =CH$_3$, $a_5$ =CH$_3$)
Melting point: 118°–119° C. (hexane)

| | Elemental analysis for $C_{19}H_{27}NOS_2$: | | | |
|---|---|---|---|---|
| | C (%) | H (%) | N (%) | S (%) |
| Calculated: | 65.29 | 7.79 | 4.01 | 18.34 |
| Found: | 65.41 | 7.96 | 4.01 | 18.60 |

EXAMPLE 47

Compound: 4-(3,5-di-tert-butyl-4-hydroxyphenyl)-5-ethyl-2-methylthiothiazole. ( $a_4$ =CH$_2$CH$_3$, $a_5$ =CH$_3$)
Melting point: 115°–116° C. (hexane)

| | Elemental analysis for $C_{20}H_{29}NOS_2$: | | | |
|---|---|---|---|---|
| | C (%) | H (%) | N (%) | S (%) |
| Calculated: | 66.07 | 8.04 | 3.85 | 17.64 |
| Found: | 66.17 | 8.18 | 4.11 | 17.60 |

EXAMPLE 48

Compound: 4-(3,5-di-tert-butyl-4-hydroxyphenyl)-5-isopropyl-2-methylthiothiazole.

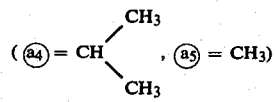

Melting point: 135°–137° C. (methanol)

| | Elemental analysis for $C_{21}H_{31}NOS_2$: | | | |
|---|---|---|---|---|
| | C (%) | H (%) | N (%) | S (%) |
| Calculated: | 66.80 | 8.27 | 3.71 | 16.98 |

-continued

Elemental analysis for $C_{21}H_{31}NOS_2$:

| | C (%) | H (%) | N (%) | S (%) |
|---|---|---|---|---|
| Found: | 66.70 | 8.37 | 3.77 | 17.20 |

EXAMPLE 49

Compound: 4-(3,5-di-tert-butyl-4-hydroxyphenyl)-5-isobutyl-2-methylthiothiazole.

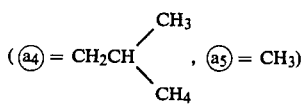

Melting point: 96°–97° C. (methanol)

Elemental analysis for $C_{22}H_{33}NOS_2$:

| | C (%) | H (%) | N (%) | S (%) |
|---|---|---|---|---|
| Calculated: | 67.42 | 8.49 | 3.58 | 16.37 |
| Found: | 67.12 | 8.71 | 3.58 | 16.59 |

EXAMPLE 50

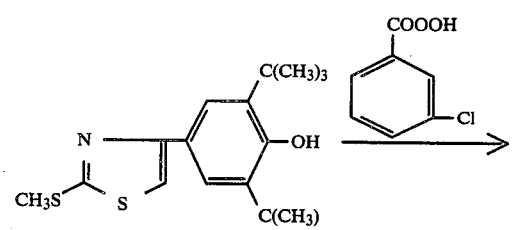

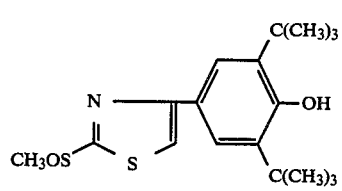

In 5 ml of chloroform was dissolved 0.8 g of 4-(3,5-di-tert-butyl-4-hydroxyphenyl)-2-methylthiothiazole and then 0.4 g of m-chloroperbenzoic acid (80%) was added portionwise to the solution with stirring. After 30 minutes since then, the reaction mixture was washed with an aqueous 5% sodium hydrogencarbonate solution and the chloroform layer was concentrated. The crystals thus obtained were recrystallized from hexane to provide 0.45 g of 4-(3,5-di-tert-butyl-4-hydroxyphenyl)-2-methylsulfinylthiazole.

Melting point: 124°–125° C.

Elemental analysis for $C_{18}H_{25}NO_2S_2$:

| | C (%) | H (%) | N (%) | S (%) |
|---|---|---|---|---|
| Calculated: | 61.50 | 7.17 | 3.98 | 18.24 |
| Found: | 61.41 | 7.32 | 4.05 | 18.56 |

EXAMPLE 51

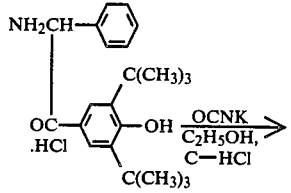

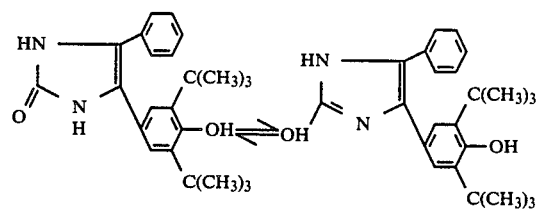

By following the same procedure as in Example 6, 4-(3,5-di-tert-butyl-4-hydroxyphenyl)-5-phenyl-2-oxo-imidazoline was produced.

Melting point: >300° C. (DMF-water)

Elemental analysis for $C_{23}H_{28}N_2O_2$:

| | C (%) | H (%) | N (%) |
|---|---|---|---|
| Calculated: | 75.79 | 7.74 | 7.69 |
| Found: | 75.70 | 7.97 | 7.85 |

EXAMPLE 52

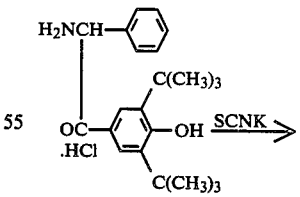

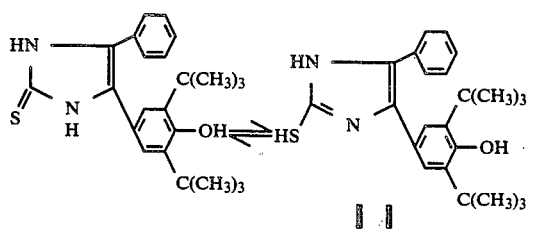

-continued

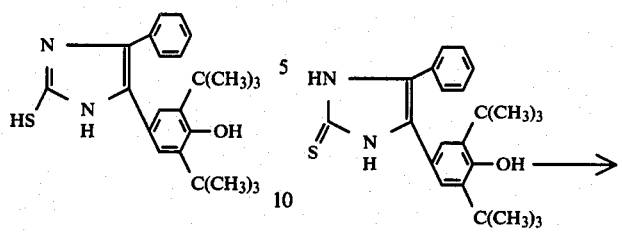

By following the same procedure as in Example 8, 4-(3,5-ti-tert-butyl-4-hydroxyphenyl)-5-phenyl-2-thioxo-4-imidazoline was produced.

Melting point: 258°–262° C. (toluene)

| Elemental analysis for $C_{23}H_{28}N_2OS$: | | | | |
|---|---|---|---|---|
| | C (%) | H (%) | N (%) | S (%) |
| Calculated: | 72.59 | 7.42 | 7.36 | 8.42 |
| Found: | 72.70 | 7.52 | 7.49 | 8.28 |

EXAMPLE 53

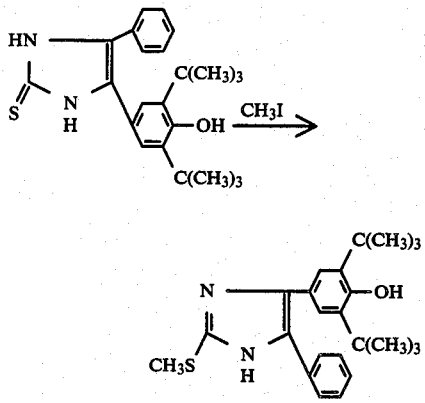

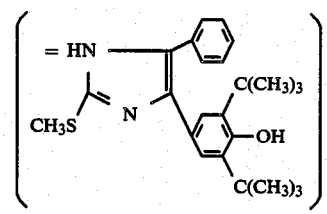

By following the same procedure as in Example 10, 4-(3,5-di-tert-butyl-4-hydroxyphenyl)-2-methylthio-5-phenylimidazole was produced.

Melting point: 129°–131° C. (toluene-hexane)

| Elemental analysis for $C_{24}H_{30}N_2OS \cdot \frac{1}{4}C_7H_8$: | | | | |
|---|---|---|---|---|
| | C (%) | H (%) | N (%) | S (%) |
| Calculated: | 74.10 | 7.67 | 6.71 | 7.67 |
| Found: | 73.64 | 7.86 | 6.42 | 7.46 |

EXAMPLE 54

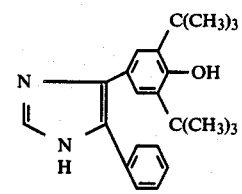

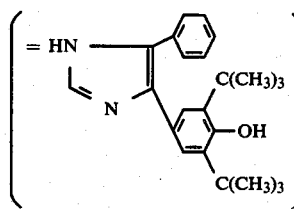

By following the same procedure as in Example 17, 4-(3,5-ditert-butyl-hydroxyphenyl)-5-phenylimidazole was produced.

Melting point: 170°–171° C. (toluene)

| Elemental analysis for $C_{23}H_{28}N_2O$: | | | |
|---|---|---|---|
| | C (%) | H (%) | N (%) |
| Calculated: | 79.27 | 8.10 | 8.04 |
| Found: | 79.16 | 8.28 | 8.06 |

EXAMPLE 55

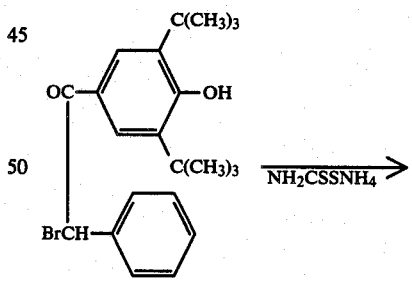

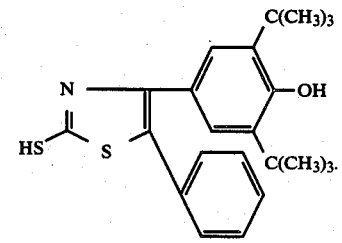

By following the same procedure as in Example 22, 4-(3,5-di-tert-butyl-4-hydroxyphenyl)-2-mercapto-5-phenylthiazole was produced.

Melting point: 168°–171° C. (tetrahydrofuran-hexane)

| Elemental analysis for C₂₃H₂₇NOS₂: | | | |
|---|---|---|---|
| | C (%) | H (%) | N (%) | S (%) |
| Calculated: | 69.48 | 6.84 | 3.52 | 16.13 |
| Found: | 69.80 | 7.10 | 3.43 | 16.22 |

EXAMPLE 56

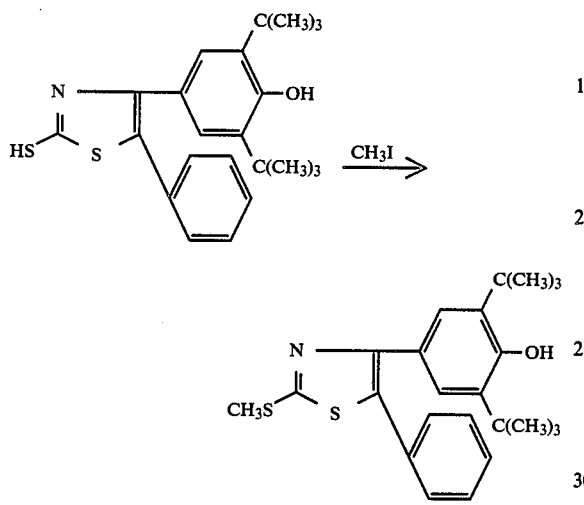

By following the same procedure as in Example 23, 4-(3,5-ditert-butyl-4-hydroxyphenyl)-2-methylthio-5-phenylthiazole.

Melting point: 135°–137° C. (hexane)

| Elemental analysis for C₂₄H₂₉NOS₂: | | | |
|---|---|---|---|
| | C (%) | H (%) | N (%) | S (%) |
| Calculated: | 70.03 | 7.10 | 3.40 | 15.58 |
| Found: | 70.30 | 7.37 | 3.44 | 15.61 |

EXAMPLE 57

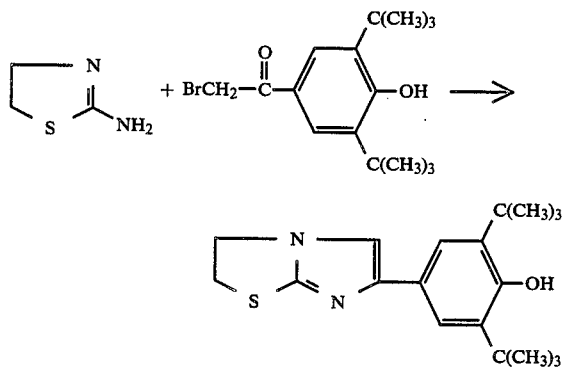

In 300 ml of methyl ethyl ketone was dissolved 10.2 g of 2-amino-2-thiazoline and after adding 32.7 g of 3,5-di-tert-butyl-4-hydroxyphenacyl bromide was added portionwise to the solution followed by stirring for 30 minutes at room temperature, the resultant mixture was refluxed for one hour. Then, the solvent was distilled off under reduced pressure, the crystals thus formed were dissolved in 200 ml of ethanol, and the solution was refluxed for 4 hours. The reaction mixture was basified with the addition of aqueous ammonia and then 200 ml of water was added to the reaction mixture to precipitate crude crystals, which were recovered by filtration and recrystallized from ethanol to provide 23.5 g of 6-(3,5-di-tert-butyl-4-hydroxyphenyl)-2,3-dihydroimidazo[2,1-b]thiazole.

Melting point: 212°–214° C.

| Elemental analysis for C₁₉H₂₆N₂OS: | | |
|---|---|---|
| | C (%) | H (%) | N (%) |
| Calculated: | 69.11 | 8.04 | 8.43 |
| Found: | 69.05 | 7.93 | 8.48 |

EXAMPLE 58

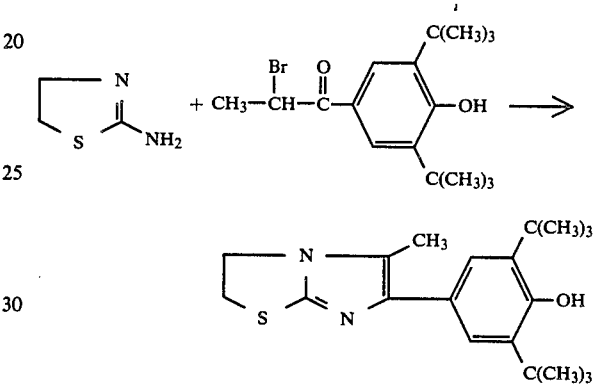

By following the same procedure as in Example 57, 6-(3,5-di-tert-butyl-4-hydroxyphenyl)-5-methyl-2,3-dihydroimidazo[2,1-b]thiazole was produced.

Melting point: 258°–261° C.

| Elemental analysis for C₂₀H₂₈N₂OS: | | |
|---|---|---|
| | C (%) | H (%) | N (%) |
| Calculated: | 69.62 | 8.22 | 8.11 |
| Found: | 69.73 | 8.19 | 8.13 |

EXAMPLE 59

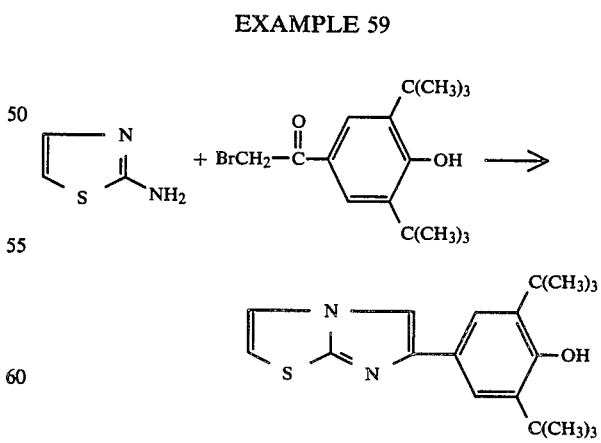

In 20 ml of ethanol were dissolved 1.2 g of 2-aminothiazole and 3.9 g of 3,5-di-tert-butyl-4-hydroxyphenacyl bromide, and the solution was refluxed for 2 hours. The reaction mixture was neutralized by the addition of aqueous ammonia and added 30 ml of water. The crystals thus precipitated were recovered by filtration and recrystallized from ethanol to provide 1.5 g of 6-(3,5-di-tert-butyl-4-hydroxyphenyl)imidazo[2,1-b]thiazole.
Melting point: 184°–185° C.

| Elemental analysis for $C_{19}H_{24}N_2OS$: | | | |
|---|---|---|---|
| | C (%) | H (%) | N (%) |
| Calculated: | 69.31 | 7.65 | 8.38 |
| Found: | 69.48 | 7.36 | 8.53 |

EXAMPLES 60–64

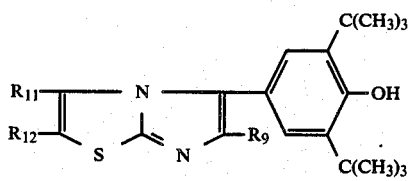

By following the same procedure as in Example 59, the following compounds were produced.

EXAMPLE 60

Compound: The compound of the above formula wherein $R_9$ is $CH_3$, $R_{11}$ is $CH_3$, and $R_{12}$ is H.
Melting point: 188°–190° C. (n-hexane-cyclohexane)

| Elemental analysis for $C_{21}H_{28}N_2OS$: | | | |
|---|---|---|---|
| | C (%) | H (%) | N (%) |
| Calculated: | 70.56 | 8.03 | 7.64 |
| Found: | 70.75 | 7.92 | 7.86 |

EXAMPLE 61

Compound: The compound of the above formula wherein $R_9$ is $CH_3$, $R_{11}$ is $CH_3$, and $R_{12}$ is $CH_3$.
Melting point: 208°–210° C. (n-hexane)

| Elemental analysis for $C_{22}H_{30}N_2OS \cdot \frac{1}{4}H_2O$: | | | |
|---|---|---|---|
| | C (%) | H (%) | N (%) |
| Calculated: | 70.67 | 8.27 | 7.39 |
| Found: | 71.31 | 8.16 | 7.56 |

EXAMPLE 62

Compound: The compound of the above formula wherein $R_9$ is H, $R_{11}$ is H, and $R_{12}$ is Br.
Melting point: 174°–176° C. (n-hexane-cyclohexane)

| Elemental analysis for $C_{19}H_{23}BrN_2OS$: | | | |
|---|---|---|---|
| | C (%) | H (%) | N (%) |
| Calculated: | 56.40 | 5.92 | 6.55 |
| Found: | 56.02 | 5.69 | 6.88 |

EXAMPLE 63

Compound: The compound of the above formula wherein $R_9$ is H, $R_{11}$ is H, and $R_{12}$ is $CH_3S$.
Melting point: 131°–132° C. (n-hexane-cyclohexane)

| Elemental analysis for $C_{20}H_{26}N_2OS_2$: | | | |
|---|---|---|---|
| | C (%) | H (%) | N (%) |
| Calculated: | 63.95 | 7.09 | 7.62 |
| Found: | 64.14 | 7.00 | 7.48 |

EXAMPLE 64

Compound: The compound of the above formula wherein $R_9$ is H, $R_{11}$ is a phenyl group, and $R_{12}$ is $CH_3$.
Melting point: 229°–231° C. (n-hexane)

| Elemental analysis for $C_{26}H_{30}N_2OS$: | | | |
|---|---|---|---|
| | C (%) | H (%) | N (%) |
| Calculated: | 74.34 | 7.60 | 6.49 |
| Found: | 74.60 | 7.22 | 6.69 |

EXAMPLE 65

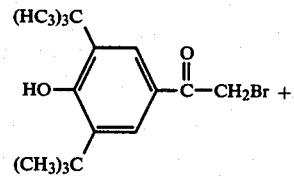

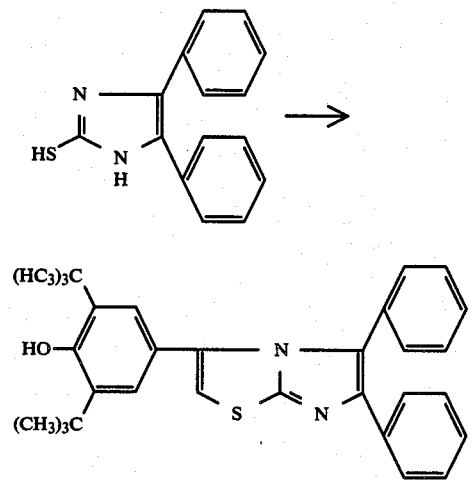

In 20 ml of ethanol was dissolved 0.11 g of metallic sodium and after adding 1 g of 4,5-diphenyl-2-mercaptoimidazole to the solution followed by stirring several minutes, 1 g of 3,5-di-tert-butylphenacyl bromide was added thereto followed by stirring for one hour at room temperature. The reaction mixture was concentrated udner reduced pressure and then water was added to the residue. The crystals thus formed were recovered by filtration, dried, dissolved in 20 ml of phosphorus oxychloride, and the solution was refluxed for 14 hours. The reaction mixture was concentrated under reduced pressure and after adding water to the residue followed by neutralization with potassium carbonate, the product was extracted with chloroform. The extract was dried and concentrated. The residue was subjected to silica gel column chromatography and the product was eluted with chloroform. The crude crystals thus obtained were recrystallized from ethanol to provide 0.8 g of 3-(3,5-di-tert-butyl-4-hydroxyphenyl)-5,6-diphenyl imidazo[2,1-b]thiazole.

Melting point: 237°–238° C.

| Elemental analysis for C₃₁H₃₂N₂OS: | | | | |
|---|---|---|---|---|
| | C (%) | H (%) | N (%) | S (%) |
| Calculated: | 77.47 | 6.57 | 5.70 | 6.48 |
| Found: | 77.46 | 6.71 | 5.83 | 6.67 |

EXAMPLE 66

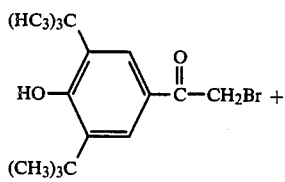

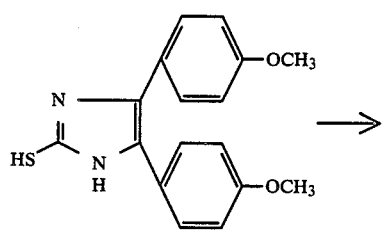

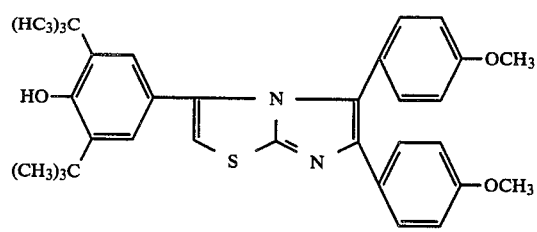

By following the same procedure as in Example 65, 3-(3,5-di-tert-butyl-4-hydroxyphenyl)-5,6-bis(p-methoxyphenyl)-imidazo[2,1-b]thiazole was produced.

Melting point: 236°–237° C.

| Elemental analysis for C₃₃H₃₆N₂SO₃: | | | | |
|---|---|---|---|---|
| | C (%) | H (%) | N (%) | S (%) |
| Calculated: | 72.92 | 6.53 | 5.32 | 6.42 |
| Found: | 73.30 | 6.71 | 5.18 | 5.93 |

EXAMPLE 67

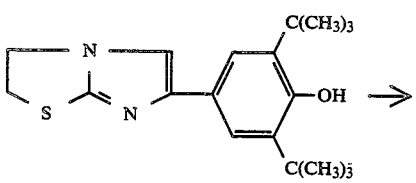

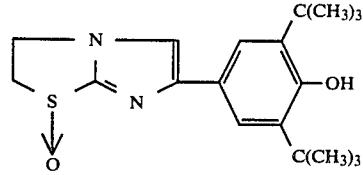

-continued

In 10 ml of chloroform was dissolved 1.6 g of 6-(3,5-di-tertbutyl-4-hydroxyphenyl)-2,3-dihydroimidazo[2,1-b]thiazole and after adding thereto 1 g of m-chloroperbenzoic acid, the mixture was stirred for 10 minutes. The reaction mixture was washed with an aqueous 5% sodium hydrogen carbonate solution, dried, and then the solvent was distilled off. The crystals thus formed were recrystallized from ethanol to provide 1.3 g of 6-(3,5-di-tert-butyl-4-hydroxyphenyl)-2,3-dihydroimidazo[2,1-b]thiazole 1-oxide as the ½ ethanol addition product.

Melting point: 211°–212° C.
Mass spectrum: m/e: 346(M+)

| Elemental analysis for C₁₉H₂₆N₂O₂S.½C₂H₅OH: | | | |
|---|---|---|---|
| | C (%) | H (%) | N (%) |
| Calculated: | 65.11 | 7.78 | 7.82 |
| Found: | 65.01 | 7.91 | 7.58 |

EXAMPLE 68

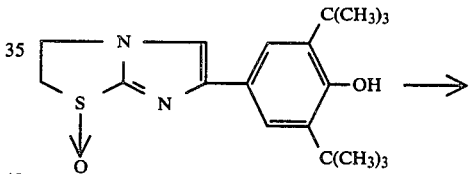

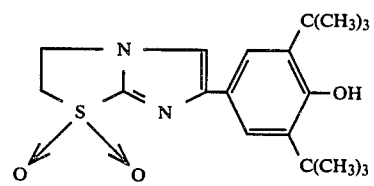

In 10 ml of chloroform was dissolved 0.6 g of 6-(3,5-di-tert-butyl-4-hydroxyphenyl)-2,3-dihydroimidazo[2,1-b]thiazole 1-oxide and then 0.4 g of m-chloroperbenzoic acid was added to the solution. After 30 minutes, 0.4 g of m-chloroperbenzoic acid was further added to the mixture and the resultant mixture was allowed to stand for one hour. The reaction mixture was washed with an aqueous 5% sodium hydrogen carbonate solution, dried, and then the solvent thereof was distilled off. The residue was purified by silica gel chromatography using chloroform as the eluent and further recrystallized from aqueous ethanol to provide 0.2 g of 6-(3,5-di-tert-butyl-4-hydroxyphenyl)-2,3-dihydroimidazo[2,1-b]thiazole 1,1-dioxide.

Melting point: 267°–269° C.

| Elemental analysis for C₁₉H₂₆N₂O₃S: | | | |
|---|---|---|---|
| | C (%) | H (%) | N (%) |
| Calculated: | 62.77 | 7.35 | 7.60 |

| Elemental analysis for $C_{19}H_{26}N_2O_3S$: | | | |
|---|---|---|---|
| | C (%) | H (%) | N (%) |
| Found: | 62.96 | 7.23 | 7.73 |

EXAMPLE 69

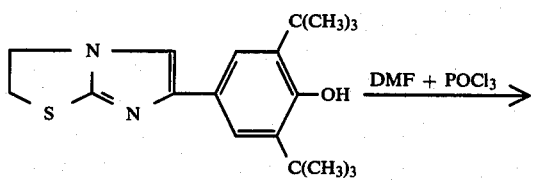

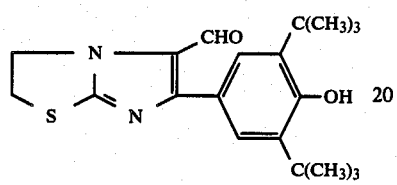

To a solution of 1.5 ml of dimethylformamide in 10 ml of chloroform was added 1.1 g of phosphorus oxychloride under ice-cooling and the mixture was allowed to stand for one hour. To the reaction mixture was added 1.5 g of 6-(3,5-di-tert-butyl-4-hydroxyphenyl)-2,3-dihydroimidazo[2,1-b]thiazole and the mixture was refluxed for 4 hours. To the reaction mixture was added 20 ml of an aqueous 10% potassium carbonate solution and the mixture was stirred for 15 minutes. The chloroform layer was dried and concentrated. The crystals thus obtained were recrystallized from ethanol to provide 1.0 g of 6-(3,5-di-tert-butyl-4-hydroxyphenyl)-5-formyl-2,3-dihydroimidazo[2,1-b]thiazole.

Melting point: 210°–212° C.

| Elemental analysis for $C_{20}H_{26}N_2O_2S$: | | | |
|---|---|---|---|
| | C (%) | H (%) | N (%) |
| Calculated: | 66.82 | 7.20 | 7.80 |
| Found: | 67.01 | 7.31 | 7.81 |

EXAMPLE 70

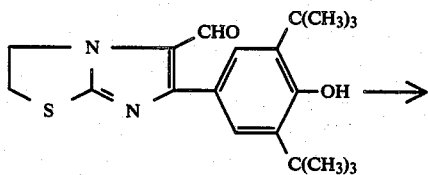

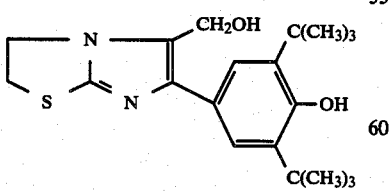

In 10 ml of ethanol was dissolved 0.4 g of 6-(3,5-di-tert-butyl-4-hydroxyphenyl)-5-formyl-2,3-dihydroimidazo[2,1-b]thiazole and after adding 40 mg of sodium borohydride to the solution, the mixture was stirred for 10 minutes. To the reaction mixture were added 0.3 ml of acetic acid and 30 ml of water, and the crystals thus precipitated were recovered by filtration and recrystallized from aqueous ethanol to provide 0.3 g of 6-(3,5-di-tert-butyl-4-hydroxyphenyl)-5-hydroxymethyl-2,3-dihydroimidazo[2,1-b]thiazole.

Melting point: 227°–229° C.

| Elemental analysis for $C_{20}H_{28}N_2O_2S$: | | | |
|---|---|---|---|
| | C (%) | H (%) | N (%) |
| Calculated: | 66.55 | 8.04 | 7.73 |
| Found: | 66.63 | 7.80 | 7.77 |

EXAMPLE 71

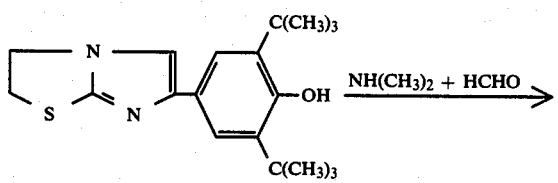

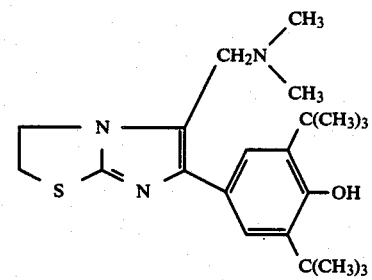

To a mixed solution of 0.9 g of an aqueous 40% dimethylamine solution, 0.5 g of an aqueous 35% formaldehyde solution, 1.5 ml of acetic acid, and 5 ml of dioxane was added 0.66 g of 6-(3,5-di-tert-butyl-4-hydroxyphenyl)-2,3-dihydroimidazo[2,1-b]thiazole and the resulting mixture was refluxed for 6 hours. The reaction mixture was concentrated under reduced pressure and the residue was mixed with 20 ml of an aqueous 10% potassium carbonate solution and extracted with chloroform. The extract was dried and concentrated, and the residue thus formed was purified by silica gel chromatography using chloroform as the eluent and further recrystallized from aqueous ethanol to provide 0.3 g of 5-dimethylaminomethyl-6-(3,5-di-tert-butyl-4-hydroxyphenyl)-2,3-dihydroimidazo[2,1-b]thiazole.¼H₂O.

Melting point: 188°–191° C.

Mass spectrum: m/e: 387(M+)

| Elemental analysis for $C_{22}H_{33}N_3OS \cdot \frac{1}{4}H_2O$: | | | |
|---|---|---|---|
| | C (%) | H (%) | N (%) |
| Calculated: | 67.49 | 8.70 | 10.48 |
| Found: | 67.39 | 8.61 | 10.72 |

EXAMPLE 72

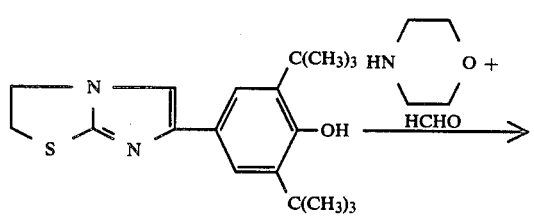

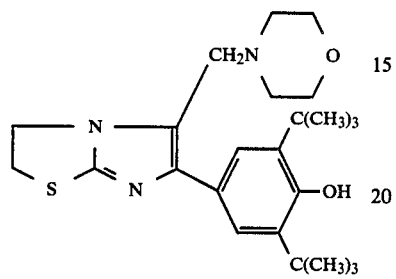

A mixture of 1.65 g of 6-(3,5-di-tert-butyl-4-hydroxyphenyl)-2,3-dihydroimidazo[2,1-b]thiazole, 1.8 g of morpholine, 1.7 g of an aqueous 35% formaldehyde solution, 1.5 ml of acetic acid, and 10 ml of dioxane was refluxed for 6 hours. The reaction mixture was concentrated udner reduced pressure and to the residue was added 20 ml of an aqueous 10% potassium carbonate to precipitate crystals, which were recovered by filtration and recrystallized from methanol to provide 0.85 g of 6-(3,5-di-tert-butyl-4-hydroxyphenyl)-5-morpholinomethyl-2,3-dihydroimidazo[2,1-b]thiazole.

Melting point: 231°-233° C.

| Elemental analysis for $C_{24}H_{35}N_3O_2S$: | | | | |
|---|---|---|---|---|
| | C (%) | H (%) | N (%) | S (%) |
| Calculated: | 67.08 | 8.32 | 9.67 | 7.35 |
| Found: | 67.10 | 8.21 | 9.78 | 7.46 |

EXAMPLE 73

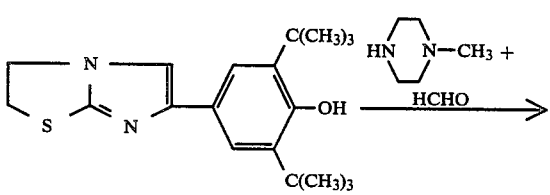

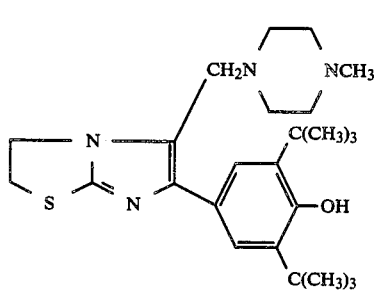

By following the same procedure as in Example 72, 6-(3,5-di-tert-butyl-4-hydroxyphenyl)-5-(4-methyl-piperazinomethyl)-2,3-dihydroimidazo[2,1-b]thiazole was produced.

Melting point: 211°-212° C.

| Elemental analysis for $C_{25}H_{38}N_4OS.H_2O$: | | | | |
|---|---|---|---|---|
| | C (%) | H (%) | N (%) | S (%) |
| Calculated: | 65.28 | 8.61 | 12.00 | 7.06 |
| Found: | 65.18 | 8.75 | 12.16 | 6.96 |

EXAMPLE 74

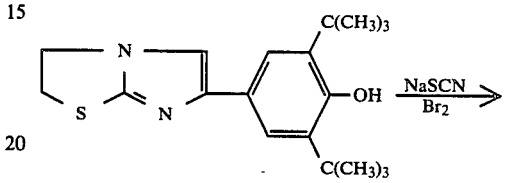

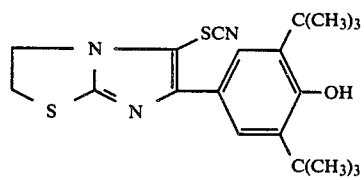

In 10 ml of acetic acid was dissolved 1.35 g of 6-(3,5-di-tert-butyl-4-hydroxyphenyl)-2,3-dihydroimidazo[2,1-b]thiazole and after adding thereto 0.64 g of sodium thiocyanate, 0.7 g of bromine was added dropwise to the solution under ice-cooling. After performing the reaction for one hour at room temperature, 30 ml of water was added to the reaction mixture to precipitate crystals, which were recovered by filtration. The crystals were added to a mixture of 20 ml of chloroform and 10 ml of an aqueous 10% potassium carbonate solution followed by stirring. The chloroform layer thus formed was dried and concentrated, and the residue thus formed was purified by silica gel column chromatography using chloroform as the eluent and further recrystallized from ethanol to provide 0.6 g 6-(3,5-di-tert-butyl-4-hydroxyphenyl)-5-thiocyanato-2,3-dihydroimidazo[2,1-b]thiazole.

Melting point: 178°-179° C.

| Elemental analysis for $C_{20}H_{25}N_3OS_2$: | | | | |
|---|---|---|---|---|
| | C (%) | H (%) | N (%) | S (%) |
| Calculated: | 62.05 | 6.50 | 10.66 | 16.84 |
| Found: | 61.98 | 6.50 | 10.84 | 16.54 |

EXAMPLE 75

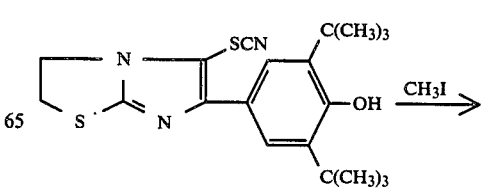

-continued

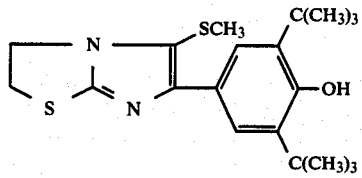

In 10 ml of methanol was dissolved 1.3 g of 6-(3,5-di-tert-butyl-4-hydroxyphenyl)-5-thiocyanato-2,3-dihydroimidazo[2,1-b]thiazole and after cooling the solution to 0° C., 0.65 g of methyl iodide was added dropwise to the solution with stirring and further a solution of 0.2 g of potassium hydroxide dissolved in a mixture of 2 ml of water and 2 ml of methanol was added dropwise to the solution. After 30 minutes, the reaction mixture was concentrated and the residue was purified by silica gel column chromatography using chloroform as the eluent and further recrystallized from ethanol to provide 0.18 g of 6-(3,5-di-tert-butyl-4-hydroxyphenyl)-5-methylthio-2,3-dihydroimidazo[2,1-b]thiazole.

Melting point: 170°–171° C.

| Elemental analysis for $C_{20}H_{28}N_2OS_2$: | | | |
|---|---|---|---|
| | C (%) | H (%) | N (%) | S (%) |
| Calculated: | 63.49 | 7.60 | 7.36 | 16.85 |
| Found: | 63.79 | 7.49 | 7.44 | 17.03 |

EXAMPLE 76

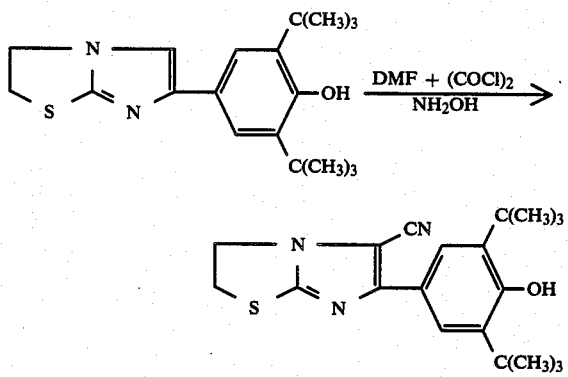

To a mixed solution of 0.5 g of dimethylformamide and 10 ml of ethylene dichloride was added dropwise a solution of 0.9 g of oxalyl chloride in 5 ml of ethylene dichloride under ice-cooling. After allowing to stand the mixture for 15 minutes at room temperature, a solution of 2 g of 6-(3,5-di-tert-butyl-4-hydroxyphenyl)-2,3-dihydroimidazo[2,1-b]thiazole dissolved in a mixture of 3 ml of dimethylformamide and 10 ml of ethylene dichloride was added dropwise to the solution and the resultant mixture was stirred for 2 hours. Then, a solution of 0.5 g of hydroxylamine hydrochloride dissolved in a mixture of 1.5 ml of dimethylformamide and 0.6 ml of pyridine was added to the reaction mixture and the resultant mixture was refluxed overnight. The reaction mixture was washed with 30 ml of an aqueous 5% sodium hydrogen carbonate solution, dried, and then concentrated. The residue thus formed was purified by silica gel column chromatography using chloroform as the eluent and further recrystallized from ethanol to provide 0.33 g of 5-cyano-6-(3,5-di-tert-butyl-4-hydroxyphenyl)-2,3-dihydroimidazo[2,1-b]thiazole.

Melting point: 207°–208° C.

| Elemental analysis for $C_{20}H_{25}N_3OS$: | | | |
|---|---|---|---|
| | C (%) | H (%) | N (%) |
| Calculated: | 67.52 | 6.92 | 11.74 |
| Found: | 67.57 | 7.09 | 11.82 |

EXAMPLE 77

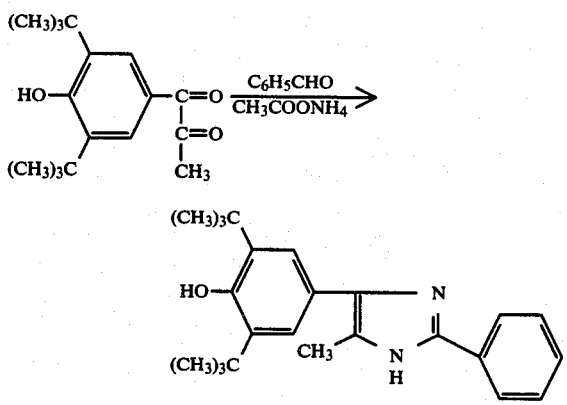

In 10ml of acetic acid was dissolved 0.6 g of 1-(3,5-di-tert-butyl-4-hydroxyphenyl)-1,2-propanedione and then after adding thereto 0.3 g of benzaldehyde and 2.2 g of ammonium acetate, the mixture was refluxed for 3 hours. The reaction mixture was concentrated and the residue formed was mixed with 20 ml of water, neutralized by the addition of concentration aqueous ammonia, and extracted with chloroform. The extract was dried and concentrated under reduced pressure. The crystals thus formed were purified by silica gel column chromatography using chloroform as the eluent and recrystallized from aqueous ethanol to provide 0.3 g of 4-(3,5-di-tert-butyl-4-hydroxyphenyl)-5-methyl-2-phenylimidazole.

Melting point: 298°–300° C.

| Elemental analysis for $C_{24}H_{30}N_2O$: | | | |
|---|---|---|---|
| | C (%) | H (%) | N (%) |
| Calculated: | 79.52 | 8.34 | 7.73 |
| Found: | 79.67 | 8.45 | 7.77 |

The clinical doses of the compounds I of this invention are usually 10–1,000 mg. per day for an adult and the medicament is administered by 2–3 times per day. The doses are properly controlled according to the condition and age of the patient.

The compounds of this invention are administered as various forms such as agents for oral administration, injections, suppositories for rectal administration, medicines for topical application, etc.

The medicaments of this invention are used as compositions prepared by blending with conventional pharmaceutical carriers or excipients by ordinary method. The tablets, capsules, granules, powders, etc., of the compounds of this invention for oral administration may contain a pharmaceutical excipient generally used in the field of art, such as calcium carbonate, calcium phosphate, starch, sucrose, lactose, talc, magnesium stearate, gelatin, polyvinyl pyrrolidone, gum arabic, sorbitol, microcrystalline cellulose, polyethylene glycol, silica, sodium laurylsulfate, etc. Moreover, the tablets may be coated by a manner well known in the art.

Furthermore, the liquid formulations for oral administration may be an aqueous or oily suspeison, a syrup, an elixir, etc., and are prepared by a conventional method.

Suppositories for rectal use are used and they may contain a formulation carrier well known in the art, such as polyethylene glycol, lanolin, cacao butter, Witepsol ® (made by Dynamite Nobel Co.), etc.

We claim:

1. A 3,5-di-tert-butyl-4-hydroxyphenyl-substituted heterocyclic compound represented by the formula

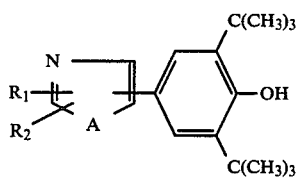

wherein $R_1$ and $R_2$, which may be the same or different, each represents a hydrogen atom, a lower alkyl group, a phenyl or naphthyl lower alkyl group, a phenyl group, a naphthyl group, a lower alkoxy-substituted phenyl or naphthyl group, or the group shown by —O—Z,

or —NH—Z wherein Z represents a hydrogen atom, a lower alkyl group, a carboxy lower alkyl group, a lower alkoxycarbonyl lower alkyl group, a phenyl or naphthyl lower alkyl group, a phenyl group, or a naphthyl group and n represents 0, 1, or 2; and A represents an oxygen atom, a sulfur atom, an imino group, a lower alkylimino group, or a 3,5-di-tert-butyl-4-hydroxyphenacylimino group

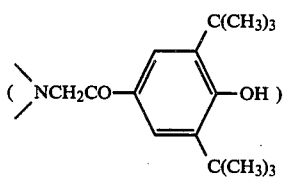

and salts thereof.

2. The heterocyclic compound of claim 1 wherein said heterocyclic compound is 4-(3,5-di-tert-butyl-4-hydroxyphenyl)-5-methyl-2-oxo-imidazolinne.

3. The heterocyclic compound of claim 1 wherein said heterocyclic compound is 4-(3,5-di-tert-butyl-4-hydroxyphenyl)-5-ethyl-2-oxo-4-imidazoline.

4. The heterocyclic compound of claim 1 wherein said heterocyclic compound is 4-(3,5-di-tert-butyl-4-hydroxyphenyl)-5-ethyl-2-methylthioimidazole.

5. The heterocyclic compound of claim 1 wherein said heterocyclic compound is 4-(3,5-di-tert-butyl-4-hydroxyphenyl)-5-methyl-2-methylthioimidazole.

6. The heterocyclic compound of claim 1 wherein said heterocyclic compound is 4-(3,5-di-tert-butyl-4-hydroxyphenyl)-5-ethylimidazole.

7. The heterocyclic compounnd of claim 1 wherein said heterocyclic compound is 4-(3,5-di-tert-butyl-4-hydroxyphenyl)-5-methylimidazole.

8. The heterocyclic compound of claim 1 wherein said heterocyclic compound is 4-(3,5-di-tert-butyl-4-hydroxyphenyl)-2-mercaptothiazole.

9. The heterocyclic compound of claim 1 wherein said heterocyclic compound is 4-(3,5-di-tert-butyl-4-hydroxyphenyl)-2-methylthiothiazole.

10. A pharmaceutical composition comprising an anti-inflammatory, anti-pyretic, analgesic, anti-arthritic, immunoregulatory or antirheumatic-effective amount of the compound of claim 1 in combination with a pharmaceutically acceptable carrier.

11. The composition of claim 10 wherein said effective amount is between about 10 and 1,000 milligrams per day.

12. A method of producing an anti-inflammatory effect in a warm-blooded animal comprising administering the composition of claim 10 to said warm-blooded animal.

13. A method of producing an anti-pyretic effect in warm-blooded animals comprising administering the composition of claim 10 to said warm-blooded animal.

14. A method producing an analgesic effect in warm-blooded animals comprising administering the composition of claim 10 to said warm-blooded animal.

15. A method of producing an anti-arthritic effect in warm-blooded animals comprising administering the composition of claim 10 to said warm-blooded animal.

16. A method of producing an immunoregulatory effect in warm-blooded animals comprising administering the composition of claim 10 to said warm-blooded animals.

* * * * *